US012600936B2

(12) United States Patent
Hirata et al.

(10) Patent No.: US 12,600,936 B2
(45) Date of Patent: Apr. 14, 2026

(54) IMAGE CAPTURING DEVICE FOR OBSERVING A SAMPLE HOUSED IN A CONTAINER TO WHICH IDENTIFICATION INFORMATION IS ATTACHED, IMAGE CAPTURING SYSTEM, AND CONTROL METHOD

(71) Applicant: Evident Corporation, Tatsuno-machi (JP)

(72) Inventors: Tadashi Hirata, Nagano (JP); Koh Mohri, Nagano (JP)

(73) Assignee: Evident Corporation, Kamiina-Gun (JP)

( * ) Notice: Subject to any disclaimer, the term of this patent is extended or adjusted under 35 U.S.C. 154(b) by 562 days.

(21) Appl. No.: 18/116,775

(22) Filed: Mar. 2, 2023

(65) Prior Publication Data

US 2023/0203423 A1 Jun. 29, 2023

Related U.S. Application Data

(63) Continuation of application No. PCT/JP2021/032692, filed on Sep. 6, 2021.

(30) Foreign Application Priority Data

Sep. 17, 2020 (JP) ................................. 2020-156038

(51) Int. Cl.
*G02B 21/00* (2006.01)
*C12M 1/34* (2006.01)
(Continued)

(52) U.S. Cl.
CPC ......... *C12M 41/46* (2013.01); *G02B 21/0088* (2013.01); *G02B 21/06* (2013.01);
(Continued)

(58) Field of Classification Search
CPC .. G02B 21/0088; G02B 21/06; G02B 21/367; G02B 21/00; G02B 21/0004;
(Continued)

(56) References Cited

U.S. PATENT DOCUMENTS

| | | | |
|---|---|---|---|
| 2002/0097451 A1 | 7/2002 | Lassen | |
| 2008/0095424 A1 | 4/2008 | Iki et al. | |
| 2018/0275388 A1 | 9/2018 | Zou et al. | |

FOREIGN PATENT DOCUMENTS

| | | | | |
|---|---|---|---|---|
| EP | 3111372 B1 | * | 2/2022 | ........... G02B 21/365 |
| JP | H05215969 A | | 8/1993 | |

(Continued)

OTHER PUBLICATIONS

International Search Report (ISR) (and English translation thereof) dated Nov. 16, 2021, issued in International Application No. PCT/JP2021/032692.

(Continued)

*Primary Examiner* — Arnel C Lavarias
(74) *Attorney, Agent, or Firm* — Holtz, Holtz & Volek PC

(57) ABSTRACT

An image capturing device for observing a sample housed in a container includes: an image capturing unit; a light guide unit that guides light from an identification surface to the image capturing unit, the identification surface being a surface of the container different from a bottom surface of the container and to which identification information is attached; and a mobile unit that changes a relative position of the image capturing unit with respect to the container. In a first relative position in which the optical axis of the image capturing unit deviates from the container, the image capturing unit images the identification surface via the light guide unit. In a second relative position in which the optical
(Continued)

axis of the image capturing unit intersects the container, the image capturing unit images the sample via the bottom surface.

20 Claims, 18 Drawing Sheets

(51) Int. Cl.

| | |
|---|---|
| *G02B 21/06* | (2006.01) |
| *G02B 21/36* | (2006.01) |
| *G06T 5/50* | (2006.01) |
| *G06V 10/141* | (2022.01) |

(52) U.S. Cl.
CPC .............. *G02B 21/367* (2013.01); *G06T 5/50* (2013.01); *G06V 10/141* (2022.01); *G06T 2207/10056* (2013.01); *G06T 2207/20221* (2013.01)

(58) Field of Classification Search
CPC ............ G02B 21/0008; G02B 21/0032; G02B 21/006; G02B 21/26; G02B 21/36; G02B 21/361; G02B 21/362; G06T 5/50; G06T 2207/10056; G06T 2207/20221; C12M 41/46; G06V 10/41; G06V 10/10; G06V 10/12; G06V 10/14; G06K 7/10712; G06K 7/10722; G06K 7/10732; G06K 7/10742; G06K 7/10831; G06K 7/10821; G06K 7/14
USPC ....... 359/368, 362, 363, 369, 385, 388, 390, 359/391, 392, 393; 235/454, 462.01, 235/462.05, 462.13, 462.41, 462.42
See application file for complete search history.

(56) References Cited

FOREIGN PATENT DOCUMENTS

| | | | |
|---|---|---|---|
| JP | 2003513487 | A | 4/2003 |
| JP | 2006047010 | A | 2/2006 |
| JP | 2009083343 | A | 4/2009 |
| JP | 6295570 | B2 | 3/2018 |
| JP | 2018534610 | A | 11/2018 |
| WO | 2006033273 | A1 | 3/2006 |

OTHER PUBLICATIONS

Japanese Office Action dated Jun. 4, 2024 (and English translation thereof), issued in counterpart Japanese Application No. 2020-156038.

* cited by examiner

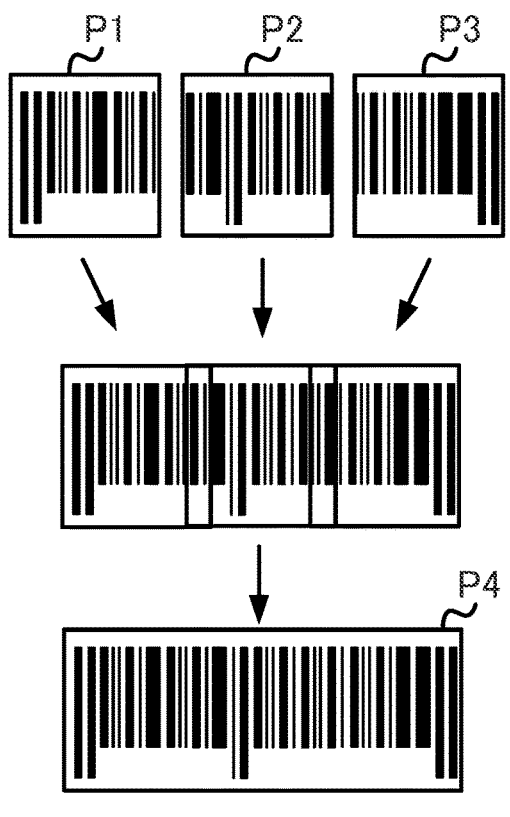
P1          P2          P3
P4
FIG. 23
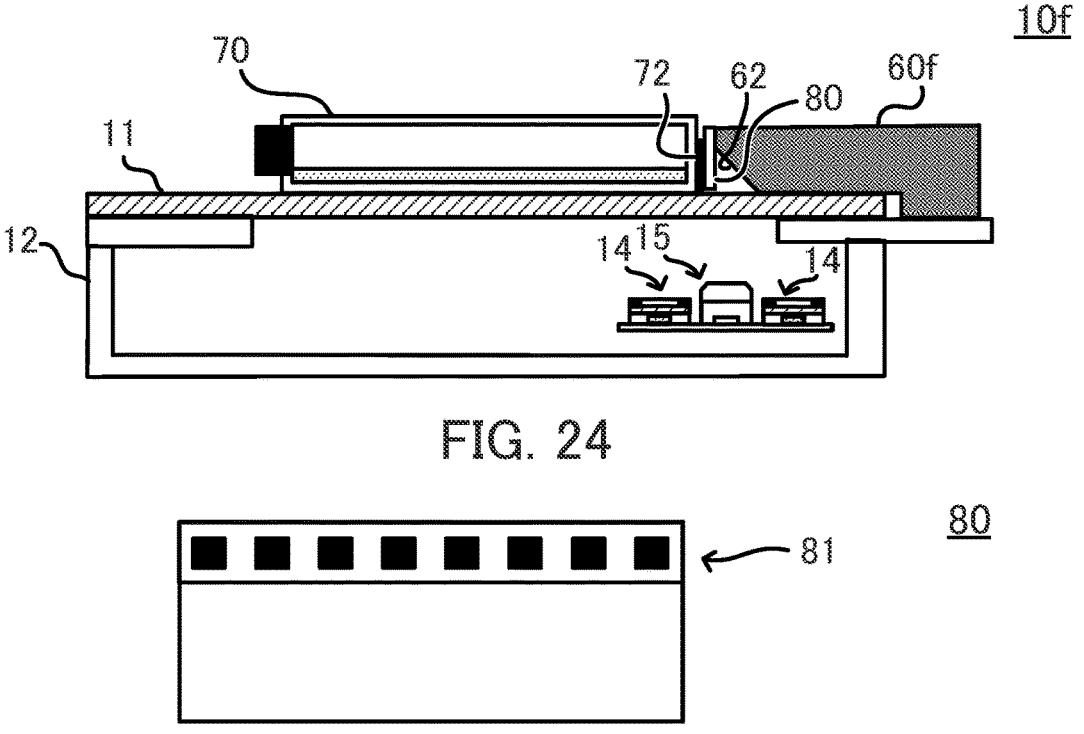
FIG. 24
FIG. 25

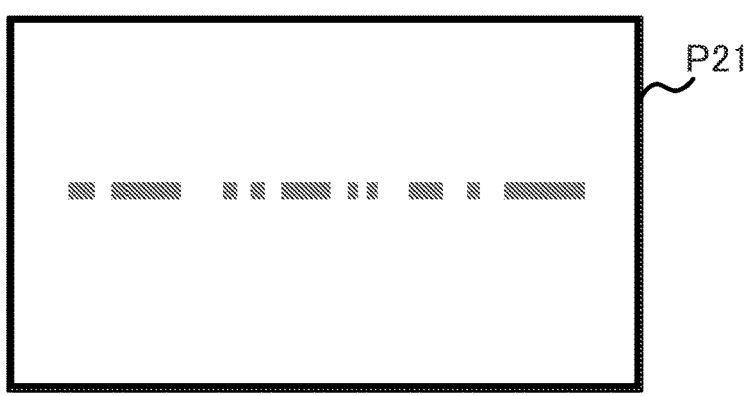
FIG. 31
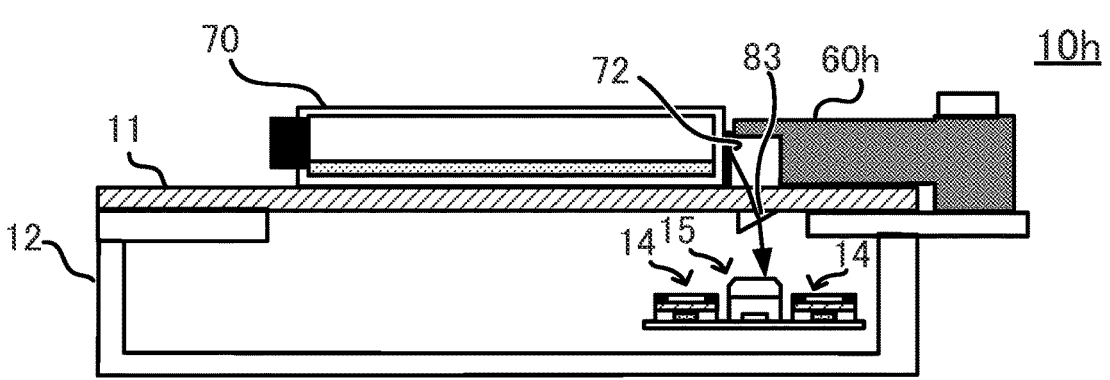
FIG. 32
| REGISTERED IDENTIFI-CATION CODE (12 CHARACTERS OR LESS) | DATE OF ISSUANCE | REGISTRANT | PRINTED |
|---|---|---|---|
| XXXPJ_K1_001 | 2020/02/13 16:34 | M.K | ※ |
| XXXPJ_K1_002 | 2020/02/13 16:37 | M.K | ※ |
| XXXPJ_K1_003 | 2020/02/20 17:34 | M.K | ※ |
| XXXPJ_K1_004 | 2020/02/20 17:37 | M.K | |
| | | | |
| | | | |
FIG. 33

IMAGE CAPTURING DEVICE FOR OBSERVING A SAMPLE HOUSED IN A CONTAINER TO WHICH IDENTIFICATION INFORMATION IS ATTACHED, IMAGE CAPTURING SYSTEM, AND CONTROL METHOD

CROSS REFERENCE TO RELATED APPLICATIONS

This application is based upon and claims the benefit of priority of the prior Japanese Patent Application No. 2020-156038, filed Sep. 17, 2020, the entire contents of which are incorporated herein by reference.

This is a Continuation Application of PCT Application No. PCT/JP2021/032692, filed Sep. 6, 2021, which was not published under PCT Article 21(2) in English.

TECHNICAL FIELD

The disclosure of the present specification relates to an image capturing device, an image capturing system, and a control method.

BACKGROUND

In culturing biological samples such as cells, various data, including images, are collected during an incubation period. These data collected during the incubation period are desirably managed in association with various culture-related information (hereinafter, simply referred to as culture information. The culture information includes, for example, a cultured cell type, a culture container type, a culturing procedure, a schedule, and the like.).

A typical method for associating an image obtained by imaging a biological sample with culture information is to use container identification information attached to a culture container. Because the container identification information is associated with the culture information in advance, the image of a biological sample and the culture information can be associated with each other via the container identification information by acquiring the container identification information attached to the culture container housing the biological sample before or after the imaging of the biological sample.

In general, a dedicated reading device (for example, a barcode reader) or a dedicated camera, or the like, provided separately from an image capturing device that is imaging a biological sample, is used to acquire container identification information. Japanese Patent Publication No. 6295570 discloses a technique for acquiring container identification information attached to a container by adjusting the focus of the image capturing device that is imaging the biological sample. According to the technique disclosed in Japanese Patent Publication No. 6295570, container identification information can be acquired without providing a dedicated configuration.

SUMMARY

An image capturing device according to one aspect of the present invention is an image capturing device for observing a sample housed in a container to which identification information is attached, from below the container, the image capturing device including: an image capturing unit including an image pickup element; a light guide unit that guides light from an identification surface to the image capturing unit, the identification surface being a surface of the container which differs from a bottom surface of the container and to which identification information is attached; and a mobile unit that changes a relative position of the image capturing unit with respect to the container, in which, after the mobile unit changes the relative position to a first relative position in which the optical axis of the image capturing unit deviates from the container, the image capturing unit images the identification surface via the light guide unit, and, after the mobile unit changes the relative position to a second relative position in which the optical axis of the image capturing unit intersects the container, the image capturing unit images the sample via the bottom surface.

An image capturing device system according to one aspect of the present invention is equipped with: the image capturing device according to the above aspect; and a control device that controls operation of the image capturing unit and the mobile unit, in which the control device records the identification information and the image of the sample in association with each other.

A control method according to one aspect of the present invention is a method for controlling an image capturing device that is equipped with an image capturing unit and a mobile unit that changes a relative position of the image capturing unit with respect to a container housing a sample, the control method including: changing the relative position to a first relative position in which an optical axis of the image capturing unit deviates from the container; imaging an identification surface via a light guide unit that guides light from the identification surface to the image capturing unit, the identification surface being a surface of the container which differs from a bottom surface of the container and to which identification information is attached; changing the relative position to a second relative position in which the optical axis of the image capturing unit intersects the container; and imaging the sample via the bottom surface.

BRIEF DESCRIPTION OF DRAWINGS

FIG. 23 is a diagram to illustrate an example of a method for creating a composite image;

FIG. 24 is a diagram to illustrate a method with which an image capturing device images an identification surface;

FIG. 25 is a diagram illustrating an example of a configuration of a transmission plate;

FIG. 31 is a diagram illustrating an example of an image of an identification surface captured by the image capturing device;

FIG. 32 is a diagram to illustrate a method with which an image capturing device images an identification surface;

FIG. 33 is a diagram illustrating an example of a screen for registering container identification information;

DESCRIPTION OF EMBODIMENTS

Incidentally, in the device disclosed in Japanese Patent Publication No. 6295570, because the container identification information and the biological sample exist coaxially, the container identification information is configured with a small dot pattern so that the presence of the container identification information does not adversely affect the image of the biological sample.

However, if the container identification information is made so small as to be difficult to visually recognize, a human cannot directly confirm the container identification information attached to the container, which is inconvenient.

In addition, because it is not possible to handle the creation of the container identification information by writing same by hand, a dedicated device for attaching the container identification information to the container is also required.

In view of the above actual circumstances, embodiments of the present invention will be described.

First Embodiment

Figure 1:
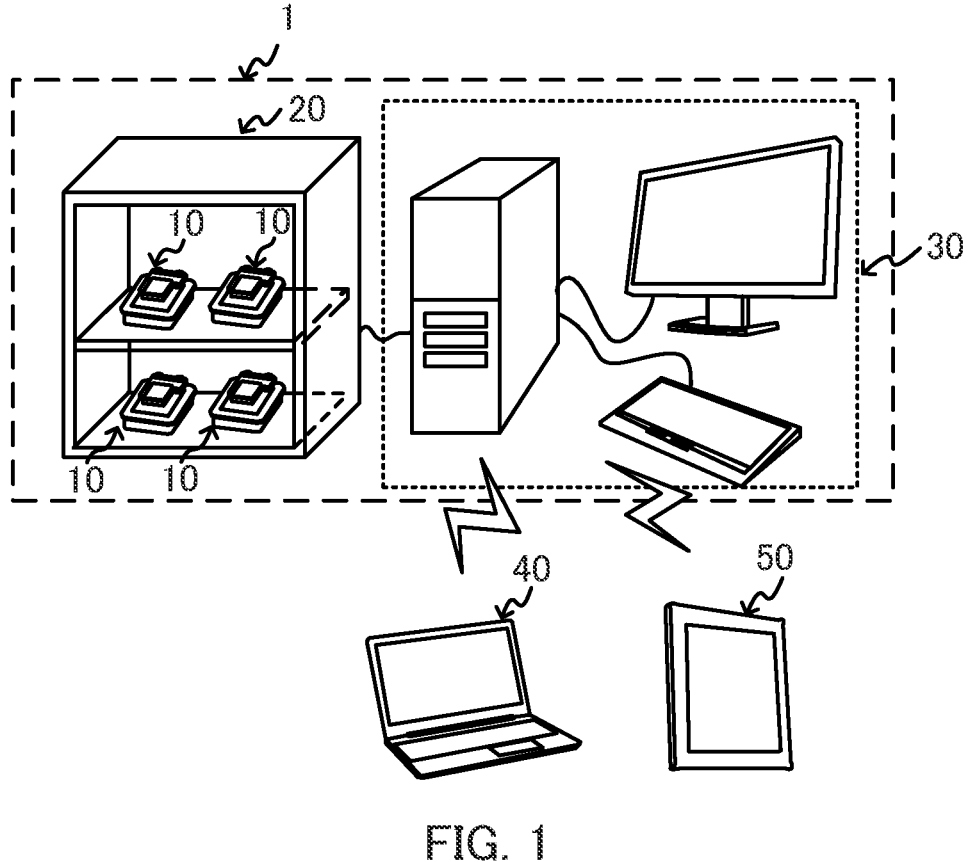
FIG. 1 is a diagram illustrating an example of a configuration of a system.
Figure 2:
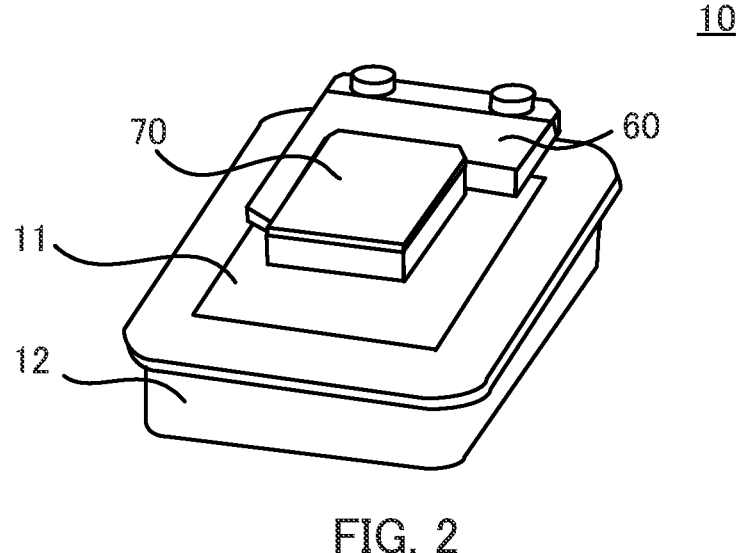
FIG. 2 is a perspective view of an image capturing device.
Figure 3:
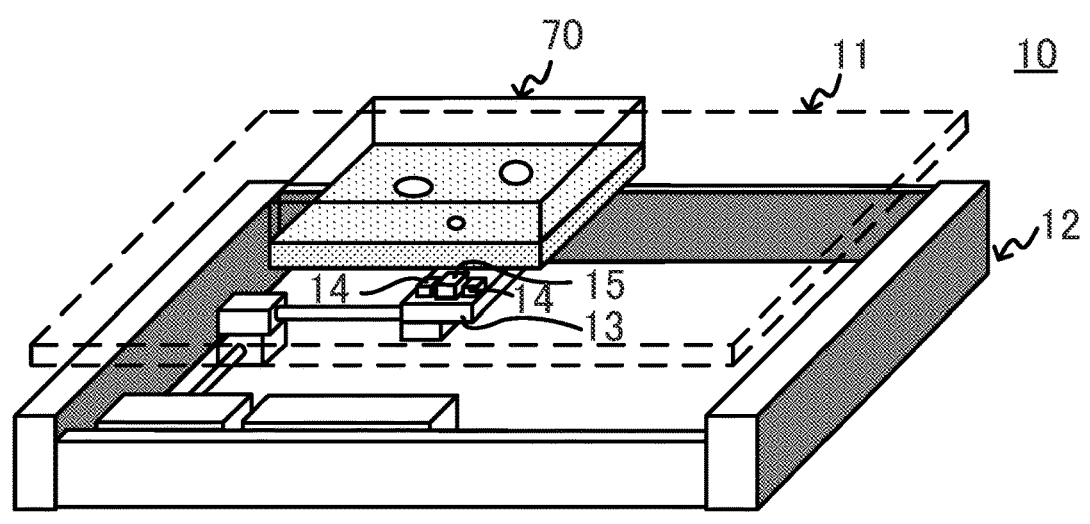
FIG. 3 is a diagram illustrating an example of a configuration of the image capturing device.
Figure 4:
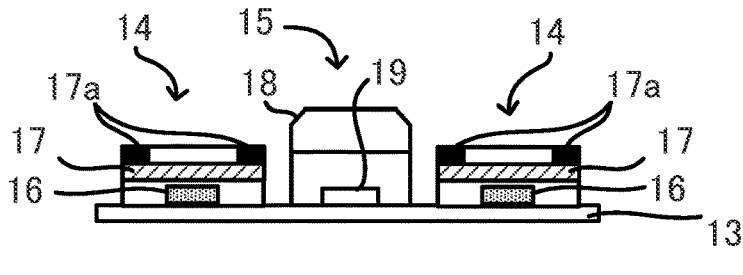
FIG. 4 is a diagram illustrating an example of a configuration of light source units and an image capturing unit.
Figure 5:
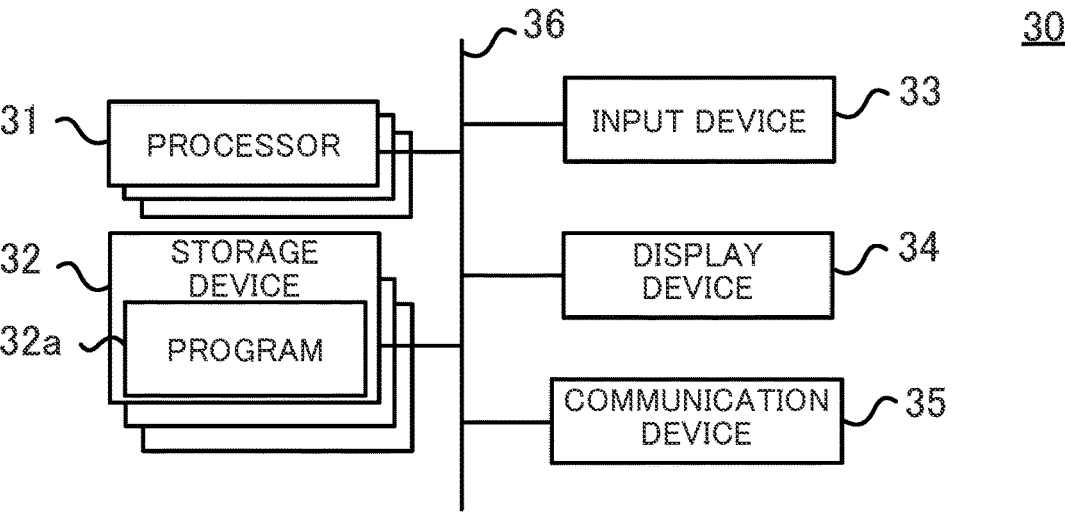
FIG. 5 is a diagram illustrating an example of a configuration of a control device.

FIG. 1 is a diagram illustrating an example of a configuration of a system 1. FIG. 2 is a perspective view of an image capturing device 10. FIG. 3 is a diagram illustrating an example of a configuration of the image capturing device 10. FIG. 4 is a diagram illustrating an example of a configuration of light source units 14 and an image capturing unit 15. FIG. 5 is a diagram illustrating an example of a configuration of a control device 30. The configuration of the system 1 will be described hereinbelow with reference to FIGS. 1 to 5.

The system 1 illustrated in FIG. 1 is an image capturing system that performs imaging while a sample that is housed in a container 70 is being cultured. The system 1 is equipped with one or more image capturing devices 10 that perform imaging of a sample housed in the container 70 from below the container 70, and a control device 30 that controls the image capturing device 10.

Each image capturing device 10 and the control device 30 are required to exchange data with each other. Therefore, each image capturing device 10 and the control device 30 may be communicably connected by wire or may be communicably connected in a wireless manner. In addition, the sample to be observed is any cultured cell, and the container 70 housing the sample is, for example, a flask. However, the container 70 is not limited to being a flask, and may be another culture container such as a dish or a well plate.

In order to capture images of a sample without removing the sample from an incubator 20, the image capturing device 10 is used in a state of being disposed in the incubator 20, as illustrated in FIG. 1, for example. More specifically, as illustrated in FIGS. 1 and 2, the image capturing device 10 is disposed in the incubator 20 in a state where the container 70 is placed on a transmission window 11 of the image capturing device 10, and acquires images of the sample in the container 70 according to an instruction from the control device 30. The transmission window 11 is a transparent top plate constituting the upper surface of the housing 12 of the image capturing device 10, and constitutes a placement surface whereon the container is placed. The transmission window 11 is made of glass or a transparent resin, for example.

As illustrated in FIG. 2, the image capturing device 10 includes a box-shaped housing 12 having a transparent transmission window 11 where the container 70 is disposed as an upper surface, and a positioning member 60 for positioning the container 70 in a predetermined position on the transmission window 11 (placement surface). Note that the positioning member 60 is fixed to the housing 12. However, the positioning member 60 can be removed as necessary, and may be replaced with another positioning member having a different shape depending on the container used.

As illustrated in FIGS. 3 and 4, the image capturing device 10 is also equipped with a stage 13 that moves inside the housing 12, a pair of light source units 14 that illuminate a sample, and an image capturing unit 15 that acquires images of the sample. The stage 13, the light source units 14, and the image capturing unit 15 are housed inside the housing 12. The light source units 14 and the image capturing unit 15 are installed on the stage 13, and move with respect to the container 70 because the stage 13 moves inside the housing 12.

The stage 13 is an example of a mobile unit of the image capturing device 10, and is a change device that changes the relative position of the image capturing unit 15 with respect to the container 70. The stage 13 is capable of moving in an X direction and a Y direction which are parallel to the transmission window 11 (the placement surface) and orthogonal to each other. However, the stage 13 may also move in a Z direction orthogonal to both the X direction and the Y direction.

Note that FIGS. 3 and 4 illustrate an example in which the light source units 14 and the image capturing unit 15 are installed on the stage 13, and, as a result, move together inside the housing 12. However, the light source units 14 and the image capturing unit 15 may move independently inside the housing 12. Further, FIGS. 3 and 4 illustrate an example in which the pair of light source units 14 are arranged on the left and right of the image capturing unit 15 such that same is sandwiched therebetween. However, the arrangement and the quantity of the light source units 14 are not limited to or by this example. For example, three or more light source units 14 may be provided on the stage 13, or only one light source unit 14 may be provided thereon.

As illustrated in FIG. 4, the light source units 14 are equipped with a light source 16 and a diffusion plate 17. The light source 16 includes, for example, a light-emitting diode (LED) or the like. The light source 16 may include a white LED or a plurality of LEDs that emit light of a plurality of different wavelengths, such as R (red), G (green), and B (blue). Light emitted from the light source 16 enters the diffusion plate 17.

The diffusion plate 17 diffuses the light emitted from the light source 16. The diffusion plate 17 is not particularly limited, and may be a frosted-type of diffusion plate having asperities formed on its surface. However, the diffusion plate 17 may be an opal-type diffusion plate having a coated surface, or may be another type of diffusion plate. Further, a mask 17a for limiting the emission region of the diffused light may be formed on the diffusion plate 17. The light emitted from the diffusion plate 17 travels in various directions.

As illustrated in FIG. 4, the image capturing unit 15 is equipped with an optical system 18 and an image pickup element 19. The optical system 18 condenses light entering the housing 12 by transmitting same through the transmission window 11. The optical system 18 is not particularly limited, but is, for example, a finite correction objective that forms an image in a finite position. However, the optical system 18 may include an infinity-corrected objective, and a finite correction optical system may be configured as the entire optical system 18. The optical system 18, which is focused on the bottom surface of the container 70 in which the sample is present, condenses light entering the housing 12 on the image pickup element 19, and thus an optical image of the sample is formed on the image pickup element 19.

The image pickup element 19 is a photosensor which converts detected light to an electrical signal. Specifically, the image pickup element 19 is an image sensor, and is, for example, a charge-coupled device (CCD) image sensor, a complementary MOS (CMOS) image sensor, or the like, although not limited thereto.

The image capturing device 10, which is configured as described above, adopts oblique illumination in order to visualize a sample in the container 70, which constitutes a phase object. Specifically, the light emitted by the light source 16 is diffused by the diffusion plate 17 and is emitted to outside the housing 12 without passing through the optical system 18. That is, the light source units 14 emit light traveling in various directions toward the outside of the housing 12 without passing through the optical system 18. Thereafter, a portion of the light emitted to outside the housing 12 is deflected above a sample by being reflected by, for example, the upper surface, or the like, of the container 70, and the sample is irradiated with a portion of the light deflected above the sample, the portion of light being transmitted through the sample and the transmission window 11 so as to enter the housing 12. Further, a portion of the light entering the housing 12 is condensed by the optical system 18 and forms an image of the sample on the image pickup element 19. That is, the optical system 18 condenses the light entering the housing 12 by transmitting same through the transmission window 11 in order to form, on the image pickup element 19, an image of the sample in the container 70 placed on the transmission window 11. Finally, the image capturing device 10 generates an image of the sample on the basis of the electrical signal outputted from the image pickup element 19 and outputs this image to the control device 30.

The control device 30 is a device for controlling the image capturing device 10. Specifically, the control device 30 may control at least the image capturing unit 15 and the stage 13 that is a mobile unit, and may further control the light source units 14. Note that the control device 30 is only required to include one or more processors and one or more non-transitory computer-readable media, and may be a general-purpose computer, for example.

More specifically, the control device 30 includes, for example, as illustrated in FIG. 5, one or more processors 31, one or more storage devices 32, an input device 33, a display device 34, and a communication device 35, which are connected via a bus 36.

Each of the one or more processors 31 is a piece of hardware including, for example, a CPU (central processing unit), a GPU (graphics processing unit), and a DSP (digital signal processor), or the like, and performs programmed processing by executing a program 32a stored in the one or more storage devices 32. Further, the one or more processors 31 may include an ASIC (application specific integrated circuit), an FPGA (field-programmable gate array), and the like.

Each of the one or more storage devices 32 may include one or more semiconductor memories and may also include one or more other storage devices, for example. The semiconductor memory may include, for example, a volatile memory such as a RAM (random access memory) and a non-volatile memory such as a ROM (read only memory), a programmable ROM, or a flash memory. The RAM may include, for example, a DRAM (dynamic random access memory) and an SRAM (static random access memory), or the like. The other storage devices may include, for example, a magnetic storage device including a magnetic disk, and an optical storage device including an optical disk.

Note that the one or more storage devices 32 are non-transitory computer-readable media and are an example of a storage unit of the system 1. At least one of the storage devices 32 stores images obtained by the image capturing device 10 imaging the sample.

The input device 33 is a device that is directly operated by a user. Examples thereof include a keyboard, a mouse, and a touch panel. Examples of the display device 34 include a liquid crystal display, an organic EL display, and a CRT (cathode ray tube) display, or the like. The display may include a built-in touch panel. The communication device 35 may be a wired communication module or a wireless communication module.

Note that the configuration illustrated in FIG. 5 is an example of the hardware configuration of the control device 30, and the control device 30 is not limited to this configuration. The control device 30 is not limited to a general-purpose device and may be a dedicated device.

The control device 30, which is configured as described above, transmits an instruction to acquire an image to the image capturing device 10 installed in the incubator 20 and receives the image acquired by the image capturing device 10. The control device 30 may display the image acquired by the image capturing device 10, on a display device 34 included in the control device 30. Thus, the system 1 may function as an observation system enabling a user to observe a sample being cultured. Note that the control device 30 may communicate with client terminals (client terminal 40 and client terminal 50) illustrated in FIG. 1, and may display the image acquired by the image capturing device 10 on a display device included in the client terminal.

Figure 6:
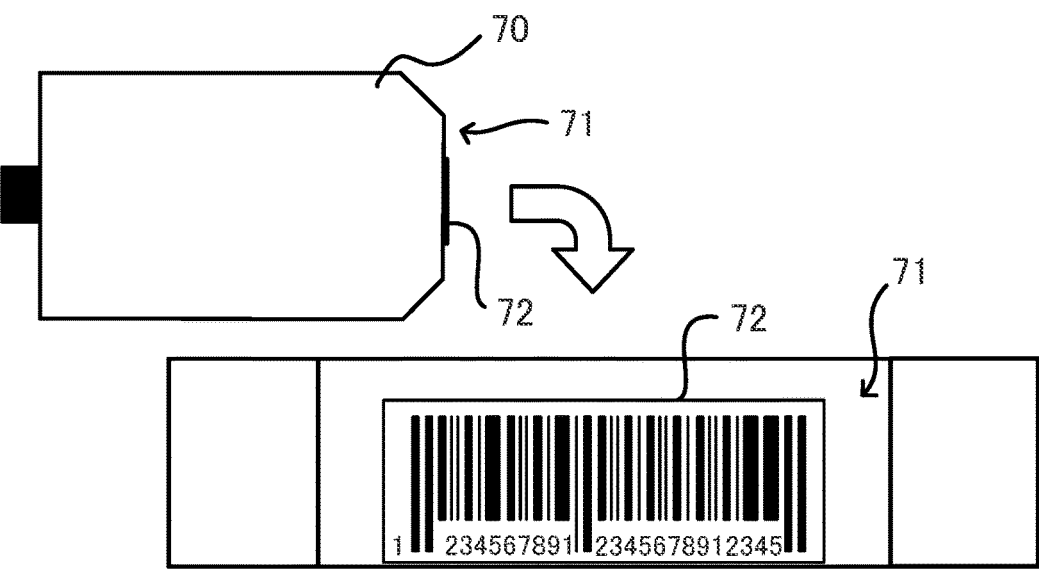
FIG. 6 is a diagram illustrating an example of a configuration of a culture container.
Figure 7:
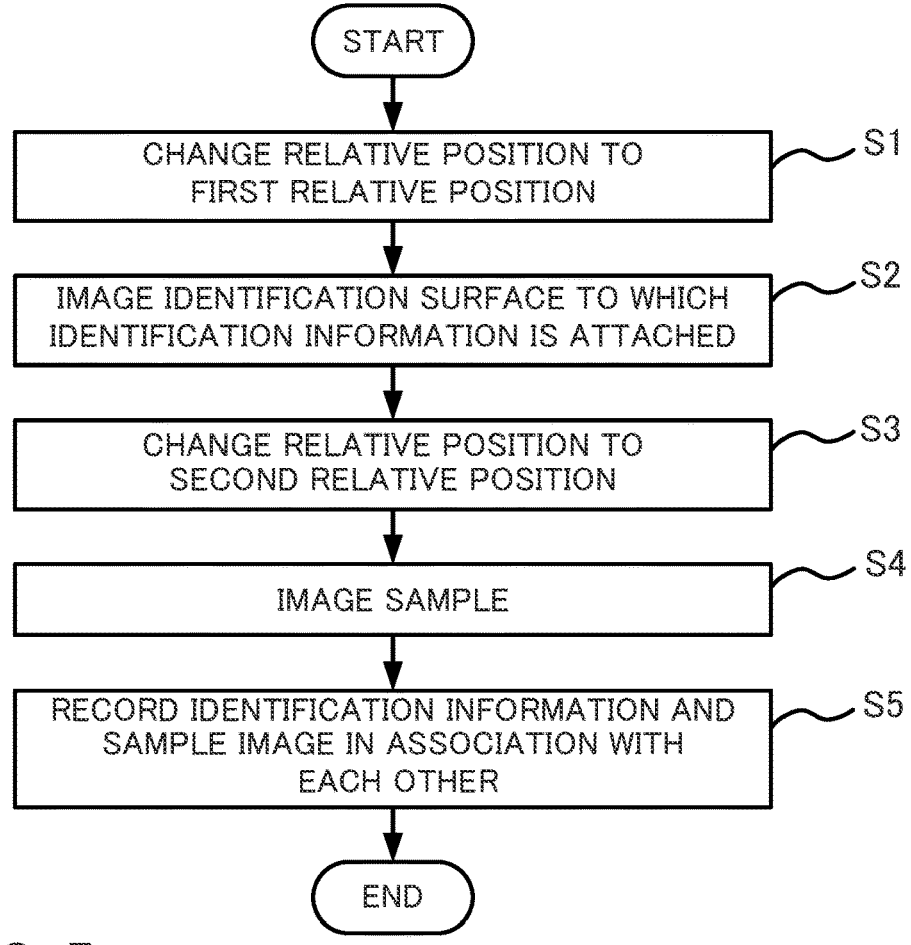
FIG. 7 is a flowchart illustrating an example of processing according to a first embodiment, which is performed by the system.
Figure 8:
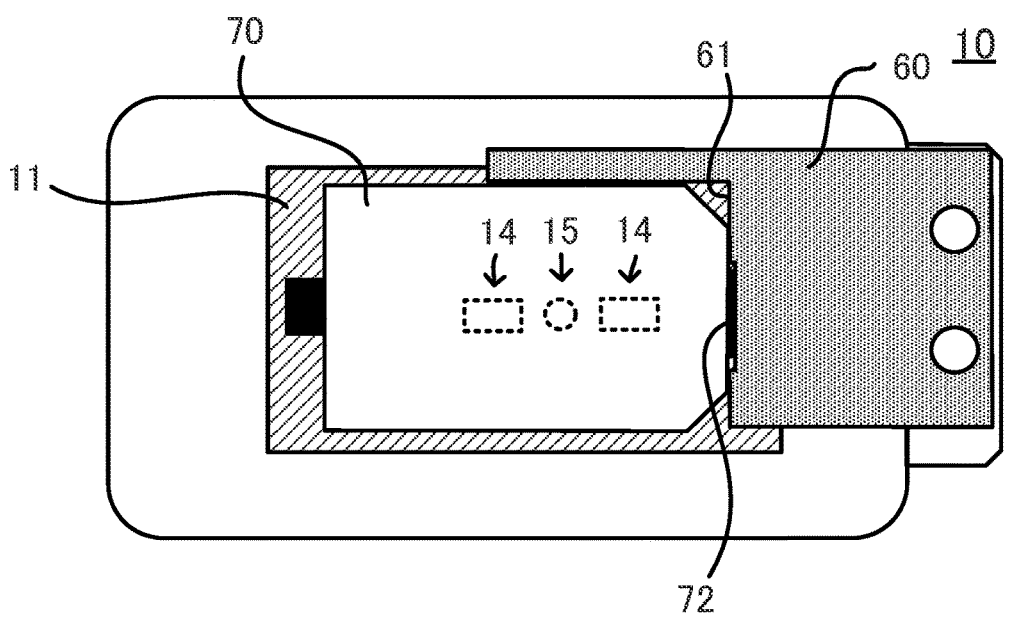
FIG. 8 is an example of a top view of the image capturing device.
Figure 9:
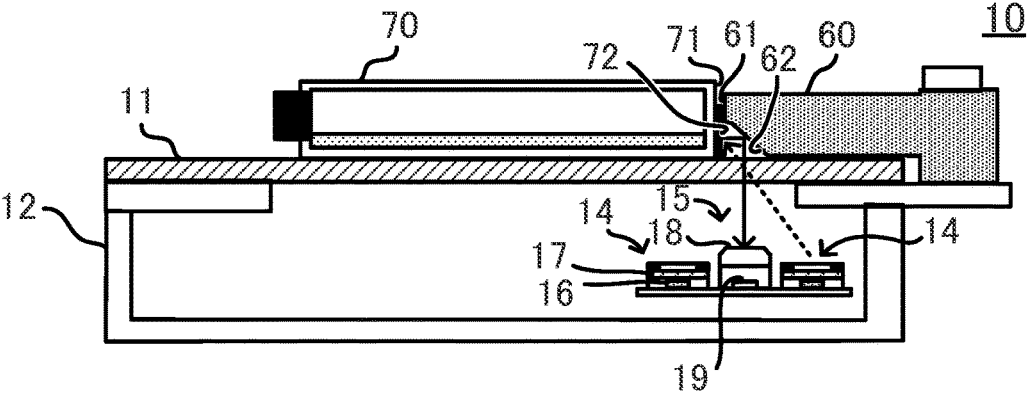
FIG. 9 is a diagram to illustrate a method with which the image capturing device images an identification surface.
Figure 10:
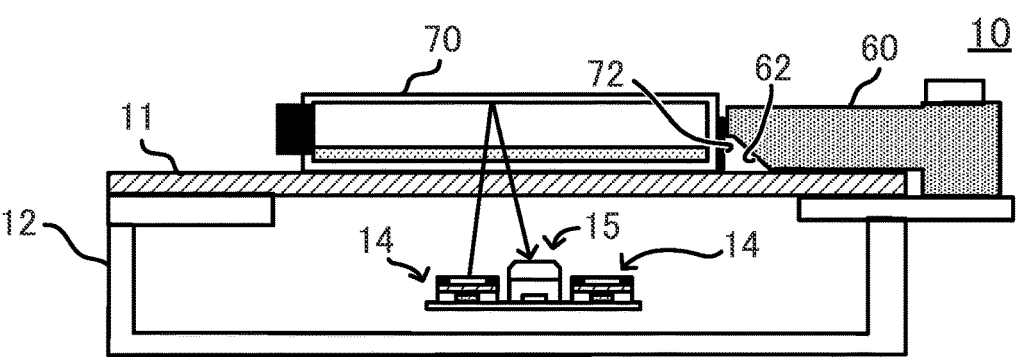
FIG. 10 is a diagram to illustrate a method with which the image capturing device images a sample.

FIG. 6 is a diagram illustrating an example of a configuration of a culture container. FIG. 7 is a flowchart illustrating an example of processing according to a first embodiment, which is performed by the system 1. FIG. 8 is an example of a top view of the image capturing device 10. FIG. 9 is a diagram to illustrate a method with which the image capturing device 10 images an identification surface. FIG. 10 is a diagram to illustrate a method with which the image capturing device 10 images a sample.

As described above, the image capturing device 10 acquires images of the sample according to an instruction from the control device 30. In the system 1, the image capturing device 10 also acquires an image of the identification surface of the container 70 to which the identification information is attached, according to the instruction from the control device 30. The control device 30 records the images of the sample acquired from the image capturing device 10 in association with the identification information 72 attached to the identification surface. It is thus possible to manage which sample in which culture container an image pertains to.

Note that, as illustrated in FIG. 6, the identification surface of the container 70 is the surface of the container 70 to which the identification information 72 for uniquely identifying the container 70 is attached. The identification information 72 is, for example, a one-dimensional code such as a barcode (registered trademark) illustrated in FIG. 6, but is not limited to a one-dimensional code. For example, same may be a two-dimensional code such as a QR code (registered trademark). In addition, a combination of numbers, characters, and other symbols may be used. The identification information 72 may be printed information or handwritten information. Further, handwritten information may be printed. Furthermore, the identification surface is a surface different from the bottom surface of the container 70 in order to avoid the identification information 72 from adversely affecting an image obtained by imaging a sample. In this example, the identification surface is a lateral surface 71 of the container 70. In addition, recording in association with the identification information is not limited to recording in association with the identification information itself, and includes recording in association with analysis information obtained by analyzing the identification information (for example, text information or the like obtained by analyzing a barcode).

Hereinafter, a method for acquiring a sample image and an identification surface image, and recording the sample image in association with identification information will be specifically described with reference to FIGS. 6 to 10.

First, as illustrated in FIG. 8, it is assumed that the container 70 is positioned in a predetermined position on the transmission window 11 as a result of the lateral surface to which the identification information 72 is attached being brought into contact with the contact surface 61 of the positioning member 60. That is, the lateral surface of the container 70 to which the identification information 72 is attached faces the positioning member 60. In this state, when the user instructs the system 1 to image a sample by using the input device 33 or the like, a program stored in the storage device 32, in the system 1, is executed by the processor 31, and the processing illustrated in FIG. 7 is performed.

When the processing illustrated in FIG. 7 is started, the system 1 first changes the relative position to the first relative position (step S1). Here, the relative position is a relative position of the image capturing unit 15 with respect to the container 70. That is, this is the position of the image capturing unit 15 when the container 70 is used as a reference. Further, the first relative position is a relative position satisfying at least a condition that the optical axis of the image capturing unit 15 deviates from the container 70.

In step S1, because the control device 30 controls operation of the stage 13, the stage 13 moves, and as a result, the relative position is changed to the first relative position by the stage 13. Specifically, as illustrated in FIG. 9, the stage 13 moves such that the optical axis of the image capturing unit 15 is located not directly below the container 70 but directly below the positioning member 60, thereby changing the relative position to the first relative position in which the optical axis of the image capturing unit 15 deviates from the container 70. More specifically, the positioning member 60 is provided with a deflection surface 62 for deflecting light to the vicinity of the contact surface 61, and the stage 13 changes the relative position to the first relative position by moving to a position in which the optical axis of the image capturing unit 15 intersects with the deflection surface 62.

Note that, as will be described subsequently, the deflection surface 62 is a light guide unit that guides, to the image capturing unit 15, light from the lateral surface 71 (identification surface) to which the identification information 72 is attached. Specifically, the deflection surface 62 is a section of the surface of the positioning member 60 and is an inclined surface inclined with respect to the optical axis. More specifically, the deflection surface 62 may be, for example, a metal thin film and a dielectric multilayer film that are formed on the surface of the positioning member 60. Further, the deflection surface 62 may be, for example, a reflective optical element attached to the substrate of the positioning member 60. The reflective optical element may be formed by coating a metal thin film or a dielectric multilayer film on the surface of a flat plate made of glass, resin, or the like, or may be formed by polishing the surface of metal to achieve high reflectance. That is, the positioning member 60 includes the light guide unit.

When the relative position is changed to the first relative position as illustrated in FIG. 9, the system 1 images the lateral surface 71 (identification surface) to which the identification information 72 is attached (step S2). Here, because the control device 30 controls operation of the light source units 14 and the image capturing unit 15, the image capturing unit 15 images the identification surface via the deflection surface 62 after the stage 13 changes the relative position to the first relative position. Note that imaging the identification surface via the deflection surface 62 means imaging the identification surface by using light which is incident on the image capturing unit 15 via the deflection surface 62.

Specifically, when the control device 30 controls light emission of the light source units 14, the image capturing device 10 irradiates the identification surface (lateral surface 71) with light (dotted line in FIG. 9) emitted from the light source units 14, as illustrated in FIG. 9. The light (the solid line in FIG. 9) reflected by the identification surface is then deflected by the deflection surface 62 so as to fall incident upon the image capturing unit 15. Because the control device 30 controls the exposure of the image capturing device 10, the image capturing device 10 generates an image of the identification surface on the basis of the light from the identification surface that falls incident upon the image capturing unit 15. The generated image is outputted to the control device 30.

When the imaging of the identification surface is completed, the system 1 changes the relative position to a second relative position (step S3). Here, the second relative position is a relative position satisfying at least a condition that the optical axis of the image capturing unit 15 intersects with the container 70.

In step S3, because the control device 30 controls operation of the stage 13, the stage 13 moves, and as a result, the relative position is changed to the second relative position by the stage 13. Specifically, as illustrated in FIG. 10, the stage 13 moves such that the optical axis of the image capturing unit 15 is located directly below the container 70, thereby changing the relative position to the second relative position in which the optical axis of the image capturing unit 15 intersects the container 70.

When the relative position is changed to the second relative position as illustrated in FIG. 10, the system 1 images the sample (step S4). Here, because the control device 30 controls operation of the light source units 14 and the image capturing unit 15, the image capturing unit 15 images the sample via the bottom surface of the container 70 after the stage 13 changes the relative position to the second relative position. Note that, here, imaging the sample via the bottom surface means imaging the sample by using the light falling incident upon the image capturing unit 15 via the bottom surface, and more specifically means imaging the sample by using the light falling incident upon the image capturing unit 15 through the bottom surface.

Specifically, when the control device 30 controls the light emission by the light source units 14 and the light exposure by the image capturing unit 15, the light emitted from the light source units 14 irradiates the sample and is transmitted through the sample and the transmission window 11 so as to enter the image capturing unit 15, as illustrated in FIG. 10. The image capturing device 10 generates an image of the sample on the basis of the light from the sample falling incident upon the image capturing unit 15. The generated image is outputted to the control device 30.

When the imaging of the sample is completed, the system 1 records the identification information and the image of the sample in association with each other (step S5). Here, the control device 30 specifies the identification information from the image of the identification surface captured by the image capturing device 10 in step S2. The control device 30 further stores the specified identification information and the image of the sample captured in step S4 in the storage device 32 in association with each other.

As described above, in the image capturing device 10 and the system 1 according to the present embodiment, the identification information can be acquired by imaging the identification surface to which the identification information is attached by using the image capturing unit 15 for imaging the sample. That is, it is possible to acquire the identification information without providing a dedicated camera or the like for imaging the identification surface. In addition, the image capturing device 10 and the system 1 are capable of acquiring the identification information attached to a surface different from the bottom surface of the container on which the sample is placed by using the light guide unit. Therefore, the presence of the identification information adversely affecting the imaging of the sample is avoidable. Thus, according to the image capturing device 10, it is possible to support the association between the identification information attached to the container 70 and the image of the sample housed in the container 70. In addition, according to the system 1, the identification information attached to the container 70 and the image of the sample housed in the container 70 can be recorded in association with each other.

Furthermore, in the image capturing device 10 and the system 1, the positioning member 60 includes the light guide unit, and thus the light guide unit is arranged in an appropriate position with respect to the container 70 simply by positioning the container 70 to abut against the positioning member 60. Therefore, the user is able to install the light guide unit in an appropriate position simply by performing work using a conventional procedure, and is able to acquire the identification information in addition to the sample image. In particular, because the position of the light guide unit with respect to the container 70 is accurately determined by including the light guide unit in the positioning member 60, the optical path length from the image capturing unit 15 to the identification surface does not greatly deviate from the assumed optical path length, and the focus adjustment can be easily performed.

Note that, although FIG. 7 illustrates an example in which the sample is imaged after the identification surface is imaged, the imaging order of the identification surface and the sample is not particularly limited to this example. Recording the identification information and the sample image in association with each other is sufficient, and the identification surface may be imaged after imaging the sample.

Figure 11:
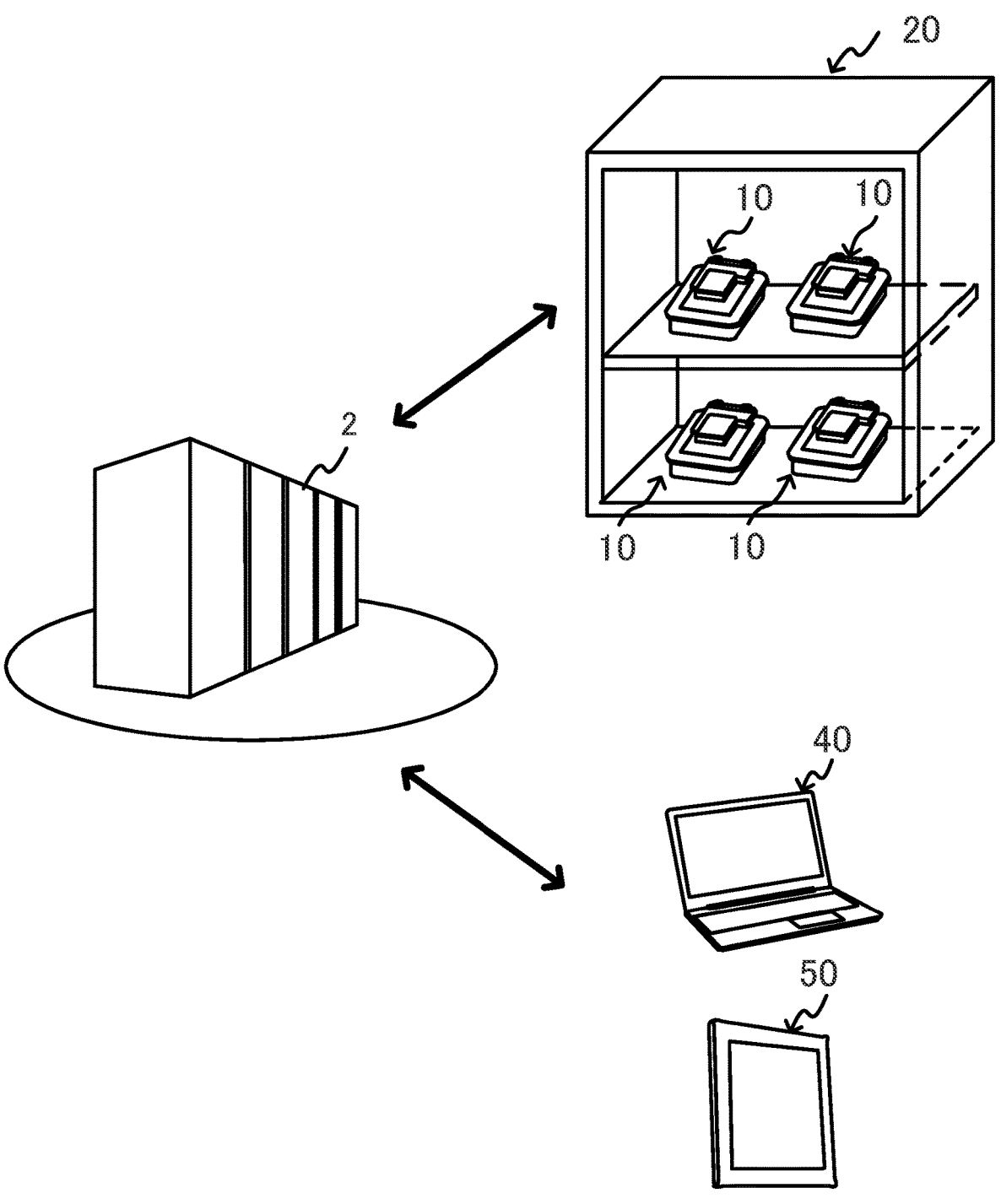
FIG. 11 is a diagram illustrating an example of a configuration of another system.

FIG. 11 is a diagram illustrating an example of a configuration of another system. In the above-described embodiment, an example in which each image capturing device 10 is controlled by the control device 30 has been described. However, a control function of the control device 30 may be incorporated into each image capturing device 10. In that case, the control device 30 may be omitted, and each image capturing device 10 may function as an IOT device that controls imaging in response to a command received via the Internet. That is, as illustrated in FIG. 11, client terminals 40 and 50 may control the imaging operation by the image capturing device 10 via a cloud server by transmitting and receiving commands to and from the cloud server 2. The image data and the identification information acquired by the image capturing device 10 are regularly or irregularly received by the cloud server. Furthermore, the image data and the identification information may be appropriately displayed on the display device included in the client terminals 40 and 50 in response to a request from the client terminals 40 and 50.

Second Embodiment

Figure 12:
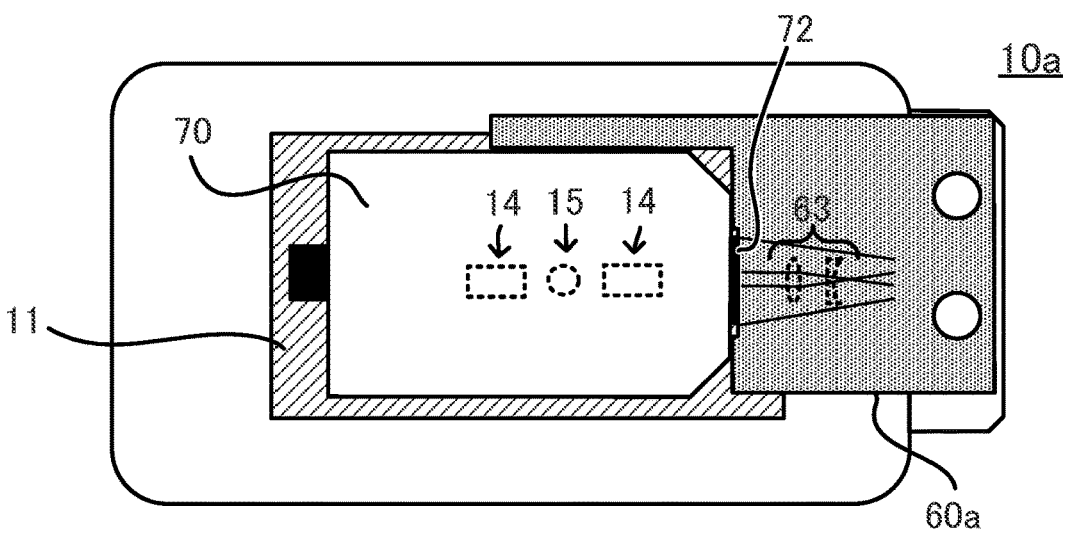
FIG. 12 is an example of a top view of an image capturing device.
Figure 13:
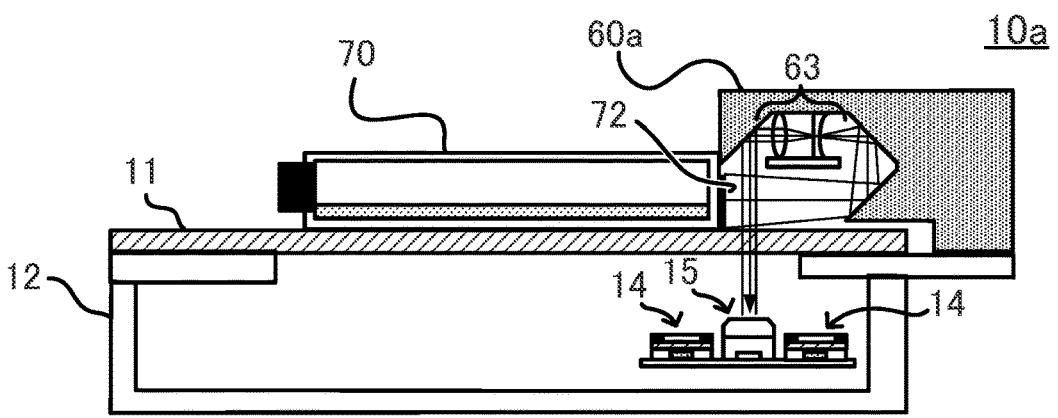
FIG. 13 is a diagram to illustrate a method with which the image capturing device images an identification surface.
Figure 14:
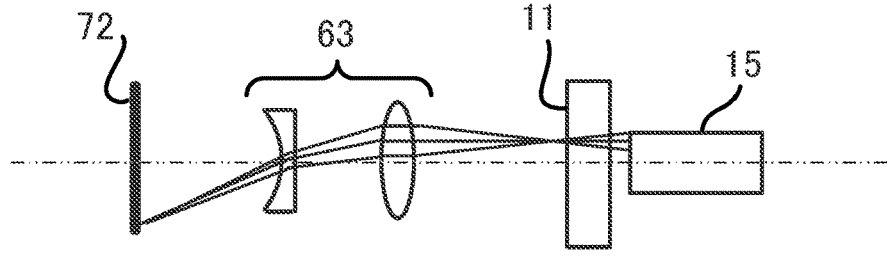
FIG. 14 is a light ray diagram of a reduction optical system.

FIG. 12 is an example of a top view of an image capturing device 10*a*. FIG. 13 is a diagram to illustrate a method with which the image capturing device 10*a* images an identification surface. FIG. 14 is a light ray diagram of a reduction optical system 63. Note that the system according to the present embodiment is the same as the system 1 except for including the image capturing device 10*a* illustrated in FIGS. 12 and 13 in place of the image capturing device 10. The image capturing device 10*a* will be described hereinbelow with reference to FIGS. 12 to 14.

The image capturing device 10*a* is also the same as the image capturing device 10 in that the image of the sample and the image of the identification surface are acquired in order to record the image of the sample and the identification information in association with each other. The imaging magnification of the image capturing unit 15 is set to a relatively high magnification suitable for satisfactorily observing a sample that is a cultured cell. For this reason, when both the sample and the identification surface are imaged by the same image capturing unit 15, only a narrow range of the identification surface to which the identification information is attached can be imaged, and the identification information may not fit in the visual field. Therefore, in the image capturing device 10*a* according to this embodiment, the light guide unit includes the reduction optical system 63. The reduction optical system 63 is an optical system that reduces the projection magnification between the identification surface to which the identification information 72 is attached and the image pickup element 19 included in the image capturing unit 15. Because the image capturing device 10*a* includes the reduction optical system 63, the entire identification information can be contained in one image.

As illustrated in FIGS. 12 and 13, the image capturing device 10*a* is different from the image capturing device 10 in that a positioning member 60*a* is included instead of the positioning member 60. The positioning member 60*a* includes a light guide unit that guides, to the image capturing unit 15, light from the identification surface to which the identification information 72 is attached. Specifically, as illustrated in FIG. 13, the positioning member 60*a* includes a plurality of (three in this example) deflection surfaces that deflect light from the identification surface, and the reduction optical system 63, which constitute the light guide unit.

As illustrated in FIG. 14, the reduction optical system 63 is a relay optical system that forms an intermediate image of the identification surface to which the identification information 72 is attached, and forms the intermediate image near the upper surface of the transmission window 11. That is, the reduction optical system 63 forms an intermediate image at the same height as the bottom surface of the container 70. The three deflection surfaces are arranged to form an optical path that turns in the height direction (the Z direction) in order to gain optical path length between the identification information 72 and the image pickup element 19.

The image capturing device 10*a* and the system according to this embodiment that includes the image capturing device 10*a* enable, by performing the processing illustrated in FIG. 7, the identification information attached to the container 70 and the image of the sample housed in the container 70 to be recorded in association with each other, similarly to the image capturing device 10 and the system 1 according to the first embodiment. Furthermore, the same is also true regarding the fact that the identification information can be acquired without providing a dedicated camera or the like for imaging the identification surface, the fact that the presence of the identification information adversely affects the imaging of the sample is avoidable, and the fact that the user is able to install the light guide unit in an appropriate position simply by performing work using a conventional procedure.

Furthermore, with the image capturing device 10*a* and the system according to this embodiment, because an image can be acquired using magnification in the first relative position which is lower than that in the second relative position, the entire identification information can be acquired using one imaging action while the cultured cell is imaged using the appropriate magnification. In addition, because the reduction optical system 63 is configured as a relay optical system, any aberrations can be satisfactorily corrected, and it is thus possible to acquire an image of the identification surface with sufficient image quality to analyze the identification information 72. Therefore, the identification information and the image of the sample can be efficiently acquired and recorded in association with each other.

Figure 15:
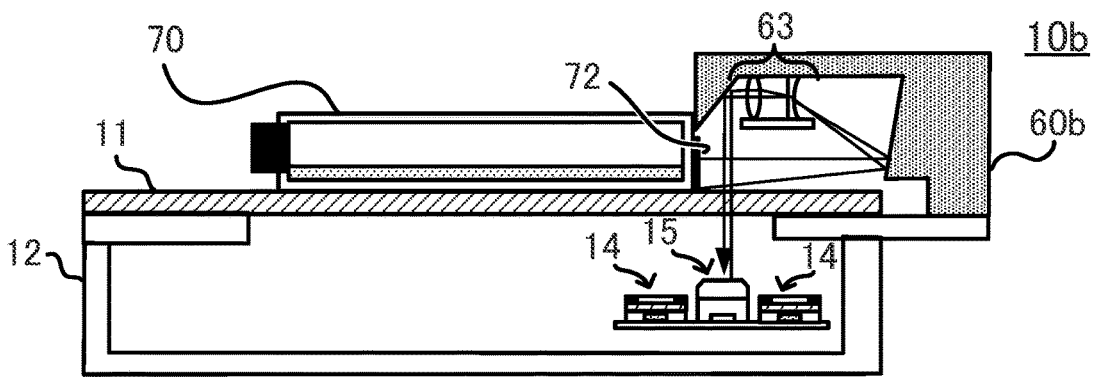
FIG. 15 is a diagram to illustrate a method with which an image capturing device images an identification surface.

FIG. 15 is a diagram to illustrate a method with which an image capturing device 10*b* images an identification surface. The image capturing device 10*b* illustrated in FIG. 15 is a modification of the image capturing device 10*a* according to the second embodiment. The system according to this embodiment may also be equipped with an image capturing device 10*b* instead of the image capturing device 10*a*.

The image capturing device 10*b* is different from the image capturing device 10*a* in being equipped with a positioning member 60*b* instead of the positioning member 60*a*. The positioning member 60*b* is the same as the positioning member 60*a* in being equipped with the reduction optical system 63, but differs from the positioning member 60*a* in that the positioning member has two deflection surfaces that deflect light from the identification surface. The two deflection surfaces form an optical path that turns in the height direction (the Z direction) in order to gain optical path length between the identification information 72 and the image pickup element 19.

The same advantageous effects as those of the image capturing device 10*a* and the system according to the second embodiment can also be afforded by the image capturing device 10*b* and the system including the image capturing device 10*b*. Furthermore, in the image capturing device 10*b*, because the light from the identification surface can be guided to the image capturing unit 15 via a smaller number of deflection surfaces than the image capturing device 10*a*, it is possible to obtain a brighter image while suppressing the light quantity loss generated on the deflection surface.

Figure 16:
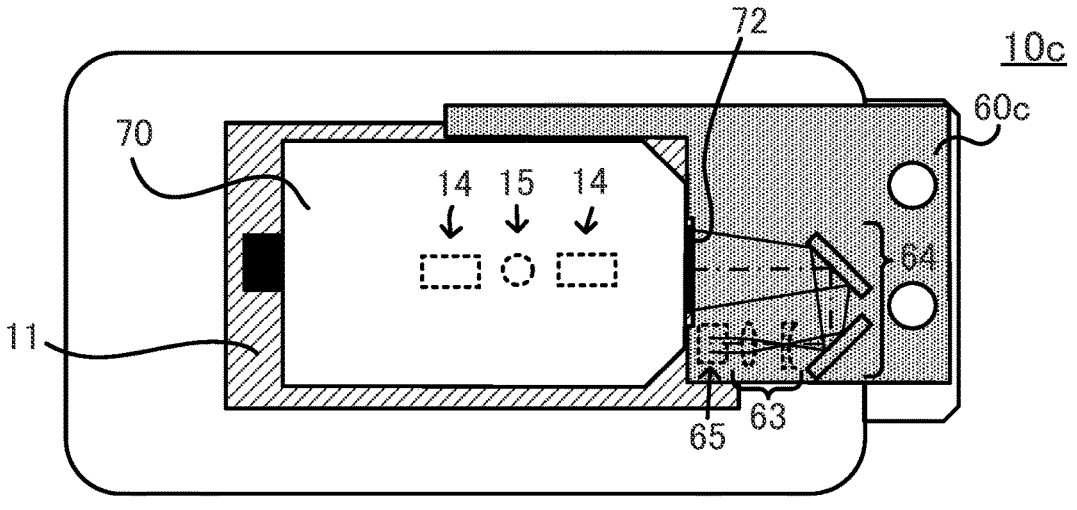
FIG. 16 is an example of a top view of an image capturing device.
Figure 17:
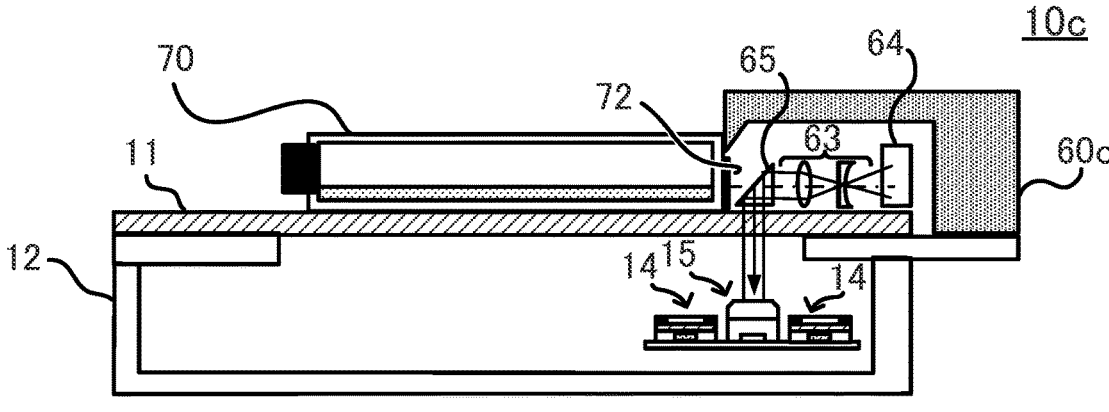
FIG. 17 is a diagram to illustrate a method with which the image capturing device images an identification surface.

FIG. 16 is an example of a top view of an image capturing device 10*c*. FIG. 17 is a diagram to illustrate a method with which the image capturing device 10*c* images an identification surface. The image capturing device 10*c* illustrated in FIGS. 16 and 17 is another modification of the image capturing device 10*a* according to the second embodiment. The system according to this embodiment may also be equipped with the image capturing device 10*c* instead of the image capturing device 10*a*.

The image capturing device 10*c* is different from the image capturing device 10*a* in being equipped with a positioning member 60*c* instead of the positioning member 60*a*. The positioning member 60*c* is the same as the positioning member 60*a* in being equipped with the reduction optical system 63, but differs from the positioning member 60*a* in also including a pair or mirrors 64 and a prism 65. The reduction optical system 63, the pair of mirrors 64, and the prism 65 constitute a light guide unit. The pair of mirrors 64 are arranged to form an optical path that turns in horizontal directions (the X and Y directions) in order to gain optical path length between the identification information 72 and the image pickup element 19. The prism 65 totally reflects the incident light via the mirrors 64 and the reduction optical system 63 and deflects the light toward the image capturing unit 15.

The same advantageous effects as those of the image capturing device 10a and the system according to the second embodiment can also be afforded by the image capturing device 10c and the system including the image capturing device 10c. Furthermore, in the image capturing device 10c and the system including the image capturing device 10c, it is possible to avoid overlapping of optical paths in the height direction by turning the optical paths in a horizontal direction. Therefore, it is not necessary to take into account the overlapping of optical paths, and the visual field can be easily secured in the height direction.

Figure 18:
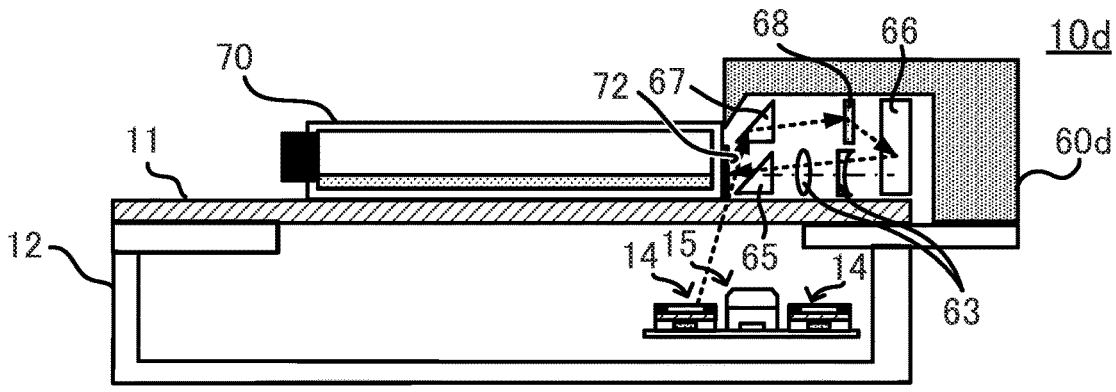
FIG. 18 is a diagram to illustrate a method with which an image capturing device images an identification surface.

FIG. 18 is a diagram to illustrate a method with which an image capturing device 10d images an identification surface. The image capturing device 10d illustrated in FIG. 18 is yet another modification of the image capturing device 10a according to the second embodiment, and is a modification of the image capturing device 10c. The system according to this embodiment may also be equipped with the image capturing device 10d instead of the image capturing device 10a.

The image capturing device 10d is different from the image capturing device 10c in being equipped with a positioning member 60d instead of the positioning member 60c. The positioning member 60d is equipped with a light guide unit configured from the reduction optical system 63, a mirror 66, and the prism 65, and is the same as the positioning member 60c in that the reduction optical system 63 and the mirror 66 form an optical path that turns in horizontal directions between the identification surface and the image capturing unit 15. In the image capturing device 10c, as a result of forming the optical path that turns in horizontal directions, the identification surface is farther away from the light source units 14 in comparison with the image capturing device 10a and the image capturing device 10b, and thus, the illumination efficiency decreases. In view of this point, the image capturing device 10d is further equipped with a prism 67 and a diffusion plate 68. The light emitted from light source units 14 is deflected toward the diffusion plate 68 by the prism 67, and is diffused by the diffusion plate 68. The diffused light is then reflected by the mirror 66 and guided to the identification surface to which the identification information 72 is attached. As a result, in the image capturing device 10d, the illumination efficiency can be enhanced in comparison with the image capturing device 10c that illuminates the identification surface with the light directly incident from the light source units 14.

The same advantageous effects as those of the image capturing device 10a and the system according to the second embodiment can also be afforded by the image capturing device 10d and the system including the image capturing device 10d. Furthermore, in the image capturing device 10d and the system including the image capturing device 10d, the visual field can be easily secured in the height direction by turning the optical path in a horizontal direction, and suppress a reduction in illumination efficiency.

Figure 19:
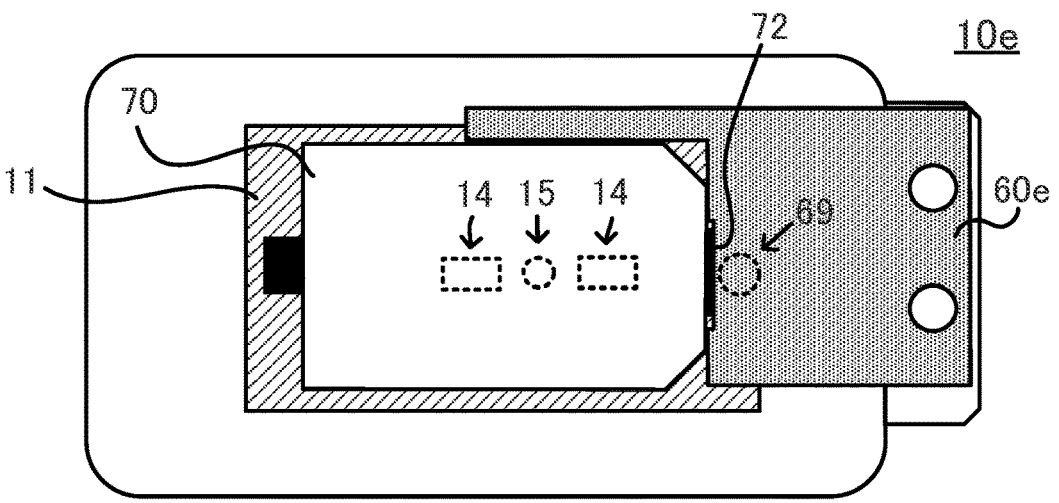
FIG. 19 is an example of a top view of an image capturing device.
Figure 20:
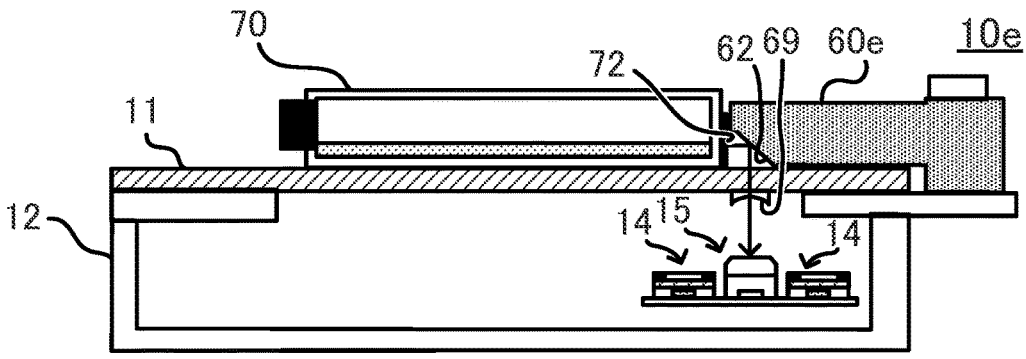
FIG. 20 is a diagram to illustrate a method with which the image capturing device images an identification surface.

FIG. 19 is an example of a top view of the image capturing device 10e. FIG. 20 is a diagram to illustrate a method with which the image capturing device 10e images an identification surface. The image capturing device 10e illustrated in FIGS. 19 and 20 is yet another modification of the image capturing device 10a according to the second embodiment. The system according to this embodiment may also be equipped with the image capturing device 10e instead of the image capturing device 10a.

The image capturing device 10e is different from the image capturing device 10a in being equipped with a positioning member 60e instead of the positioning member 60a, and in including a reduction optical system 69. The positioning member 60e may be, for example, the same as the positioning member 60 included in the image capturing device 10 according to the first embodiment. That is, as illustrated in FIG. 20, the positioning member 60e is equipped with a deflection surface 62, which is an inclined surface inclined with respect to the optical axis and which constitutes the light guide unit.

The reduction optical system 69 constitutes a light guide unit together with the deflection surface 62. That is, the positioning member 60e includes part of the light guide unit. The reduction optical system 69 is a lens having negative power, and may be, for example, a plano-concave lens as illustrated in FIG. 20. The reduction optical system 69 is provided on an optical path between the deflection surface 62 and the image capturing unit 15 in the first relative position, and specifically, may be bonded to the lower surface of the transmission window 11, as illustrated in FIG. 20, for example.

The same advantageous effects as those of the image capturing device 10a and the system according to the second embodiment can also be afforded by the image capturing device 10e and the system including the image capturing device 10e. Note that, in FIGS. 19 and 20, an example in which the reduction optical system 69 is provided in the housing 12 has been illustrated, but a reduction optical system having negative power may be provided on the transmission window 11. In addition, negative power may be afforded by forming the deflection surface 62 as a convex surface. In this case, the deflection surface having negative power can also serve as the reduction optical system.

Third Embodiment

Figure 21:
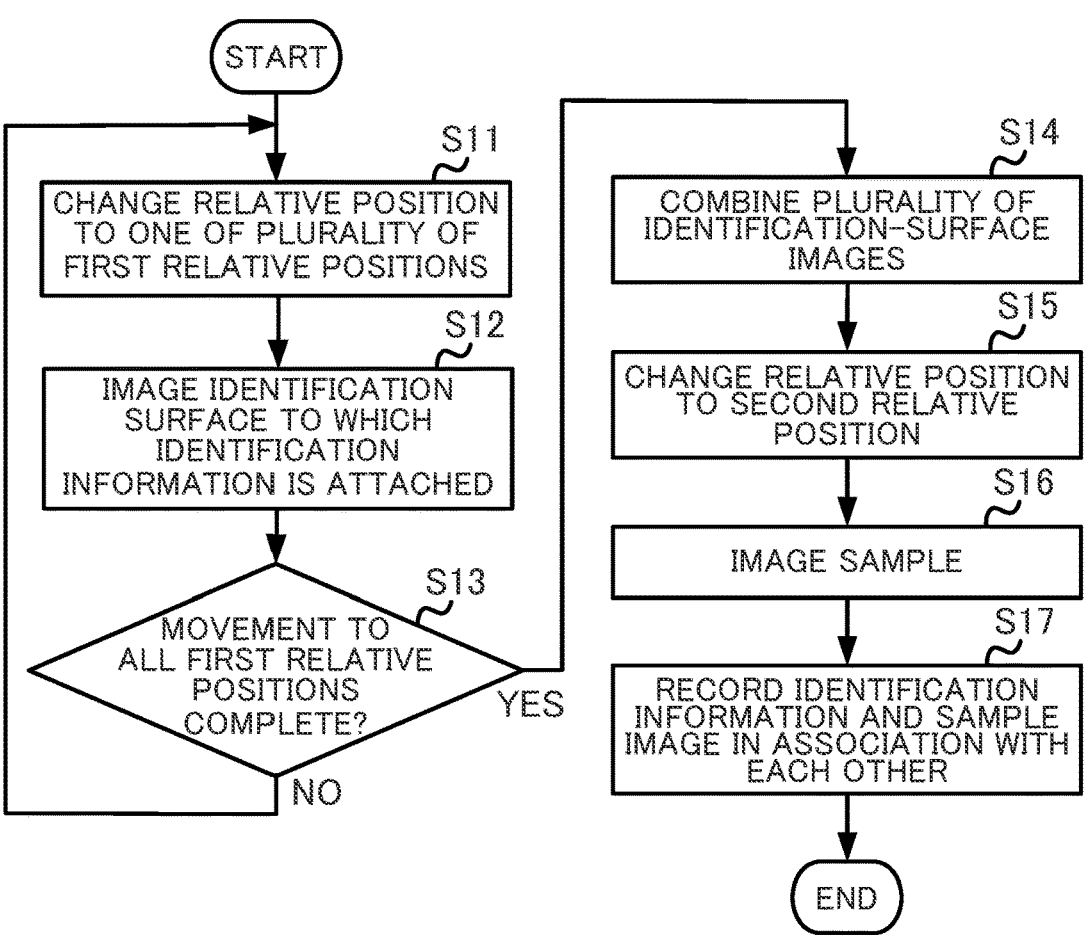
FIG. 21 is a flowchart illustrating another example of the processing performed by the system.
Figure 22:
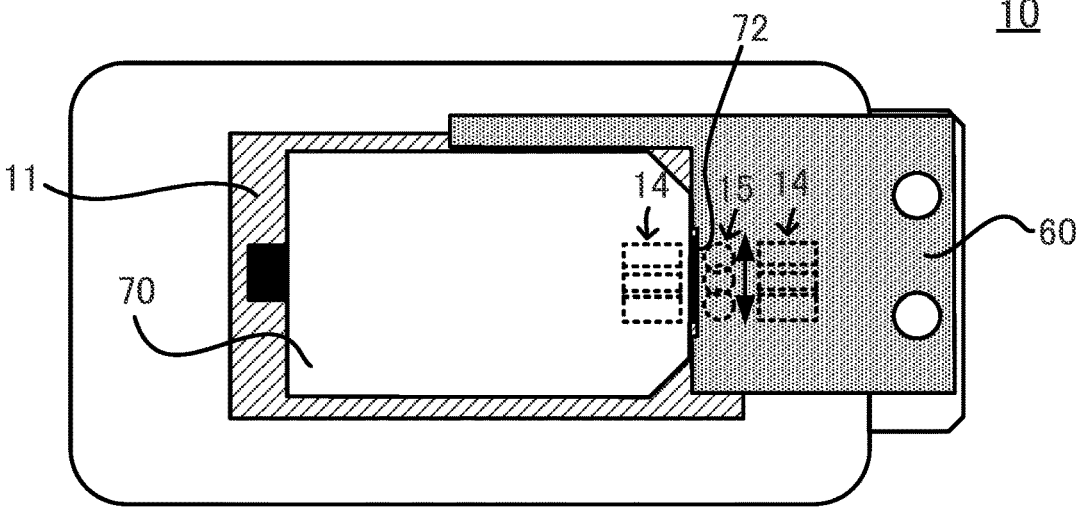
FIG. 22 is a diagram to illustrate a method with which the image capturing device images an identification surface.

FIG. 21 is a flowchart illustrating another example of the processing performed by the system. FIG. 22 is a diagram to illustrate a method with which the image capturing device 10 images an identification surface. FIG. 23 is a diagram to illustrate an example of a method for creating a composite image. In the system according to the second embodiment, an image of the entire identification information is acquired using one imaging action by imaging the identification surface at an imaging magnification which is different from that of the sample. However, in the system according to this embodiment, the entire identification information is acquired while imaging the identification surface at the same imaging magnification as that when the sample is imaged by imaging the identification surface multiple times. Hereinafter, a method for recording an image of a sample and identification information in association with each other while imaging the sample and the identification surface at the same magnification will be specifically described with reference to FIGS. 21 to 23. Note that the system according to this embodiment is, as per the system 1, equipped with the image capturing device 10 and the control device 30.

In the system according to this embodiment, a program stored in the storage device 32 is executed by the processor 31, and the processing illustrated in FIG. 21 is performed. When the processing illustrated in FIG. 21 is started, the system 1 first changes the relative position to one of a plurality of first relative positions (step S11). Here, the plurality of first relative positions is a relative position satisfying at least a condition that the optical axis of the image capturing unit 15 deviates from the container 70. Specifically, the first relative positions are relative positions different from each other at least in a direction parallel to the identification surface, and are set such that parts of the visual field of the image capturing unit 15 overlap each other between adjacent first relative positions. Note that FIG. 22 illustrates the arrangement of the image capturing units 15 in three relative positions.

When the relative position is changed to the first relative position, the system images the identification surface to which the identification information 72 is attached (step S12). This processing is the same as the processing of step S2 of FIG. 7.

When the identification surface is imaged, the system determines whether or not movement to all the first relative positions has been completed (step S13), and when it is determined that movement to all the first relative positions has not been completed (step S13: NO), the system repeats the processing of steps S11 and S12. That is, the control device 30 causes the image capturing device 10 to image the identification surface in a plurality of different first relative positions.

Thereafter, when it is determined that movement to all of the first relative positions has been performed (step S13: YES), the system combines the plurality of identification-surface images (step S14). Here, the control device 30 combines the plurality of identification-surface images captured in the plurality of first relative positions to generate a composite image in which the entire identification information 72 is captured.

Specifically, as illustrated in FIG. 23, the control device 30 uses the coordinate information of the stage 13 in the plurality of first relative positions to combine the identification-surface images P1 to P3 captured in the plurality of first relative positions, and thus generates a composite image P4. The generated composite image P4 is outputted to the control device 30. Note that, instead of the coordinate information, a composite position may be determined by pattern matching of overlapping portions of images, thus generating the composite image.

Once the composite image is generated, the system changes the relative position to a second relative position (step S15) and images the sample (step S16). These processing steps are the same as the processing of steps S3 and S4 of FIG. 7.

When the imaging of the sample is completed, the system records the identification information and the image of the sample in association with each other (step S17). Here, the control device 30 specifies identification information on the basis of the composite image generated in step S14, associates the specified identification information with the image of the sample captured in step S16, and stores the identification information and the image in the storage device 32.

So too with the image capturing device 10 and the system according to this embodiment, by performing the processing illustrated in FIG. 21, identification information can be specified without changing the imaging magnification, thus affording advantageous effects similar to those of the image capturing device and the system according to the second embodiment.

Figure 26:
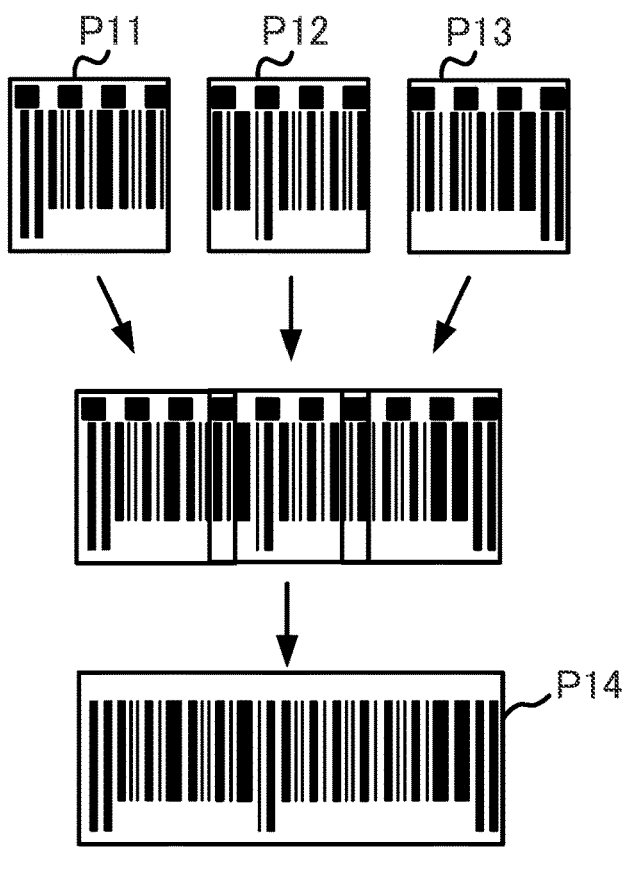
FIG. 26 is a diagram to illustrate another example of a method for creating a composite image.

FIG. 24 is a diagram to illustrate a method with which an image capturing device 10f images an identification surface. FIG. 25 is a diagram illustrating an example of a configuration of a transmission plate 80. FIG. 26 is a diagram to illustrate another example of a method for creating a composite image. The image capturing device 10f illustrated in FIG. 24 is a modification of the image capturing device according to a third embodiment. The system according to this embodiment may also be equipped with the image capturing device 10f instead of the image capturing device 10.

The image capturing device 10f differs from the image capturing device 10 in being equipped with a positioning member 60f instead of the positioning member 60. The positioning member 60f differs from the positioning member 60 in being equipped with the transmission plate 80. As illustrated in FIG. 24, the transmission plate 80 is provided to the positioning member 60f so as to be positioned between the identification surface to which the identification information 72 is attached and the deflection surface 62, in a state where the container 70 is positioned by the positioning member 60f. The transmission plate 80 is a transparent, flat plate on which a reference position marker 81 is printed as illustrated in FIG. 25. The reference position marker 81 is a set of marks (in this example, squares) of a predetermined size aligned in a certain direction at certain intervals. Note that this certain direction is desirably the same direction as the direction in which the plurality of first relative positions are aligned.

When the image capturing device 10f images the identification surface to which the identification information 72 is attached via the transmission plate 80, the control device 30 acquires the images P11 to P13 of the identification surface captured in the plurality of first relative positions, as illustrated in FIG. 26. Because the reference position marker 81 appears in a plurality of identification-surface images (image P11, image P12, and image P13), the composite image P14 can be easily obtained by determining a composite position of these images such that the reference position markers 81 overlap accurately.

The same advantageous effects as those of the image capturing device and the system according to the third embodiment can also be afforded by the image capturing device 10f and the system including the image capturing device 10f.

Figure 27:
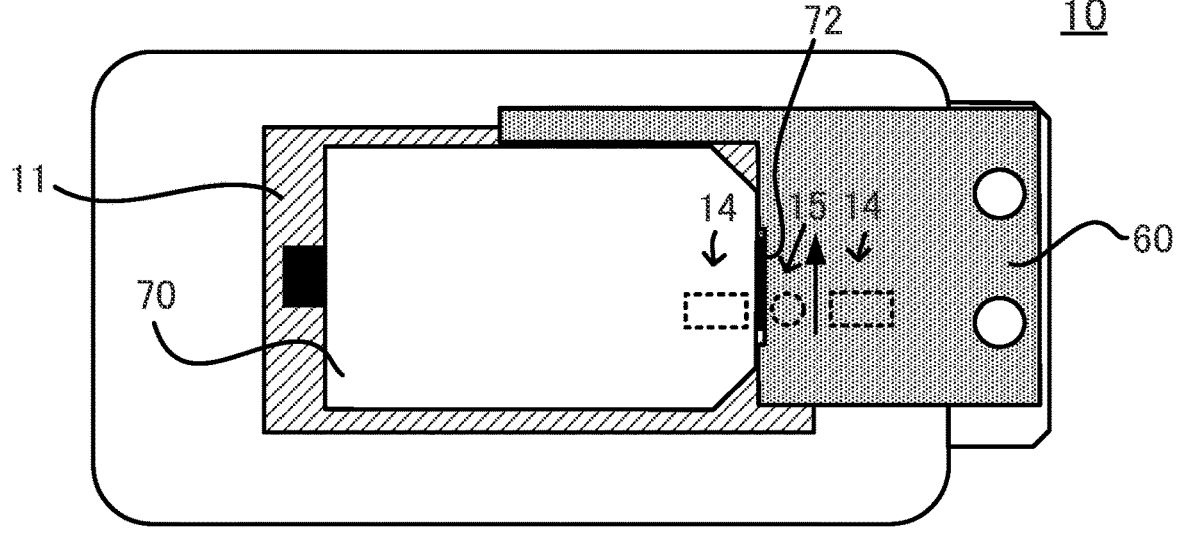
FIG. 27 is a diagram to illustrate a method with which the image capturing device scans an identification surface.
Figure 28:
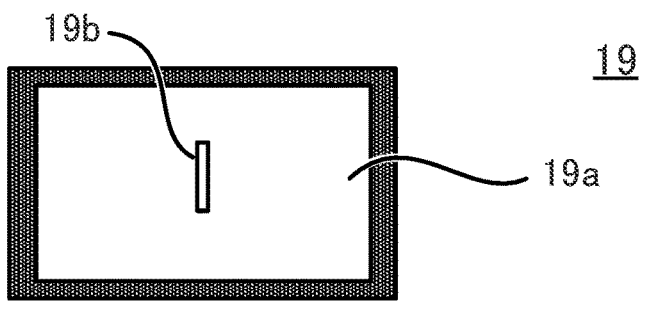
FIG. 28 is a diagram to illustrate a usage region of the image capturing unit.
Figure 29:
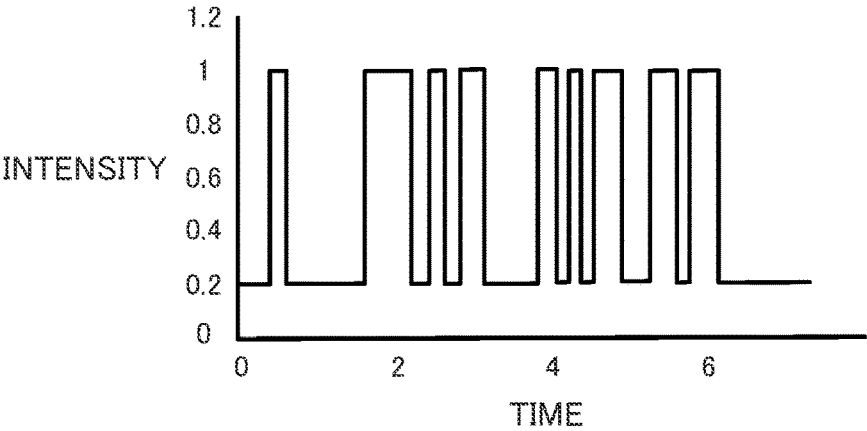
FIG. 29 is a diagram illustrating an example of a temporal intensity distribution obtained by scanning an identification surface.

FIG. 27 is a diagram to illustrate a method with which the image capturing device 10 scans an identification surface. FIG. 28 is a diagram to illustrate a usage region 19b of the image capturing unit 15. FIG. 29 is a diagram illustrating an example of a temporal intensity distribution obtained by scanning an identification surface.

In the above-described embodiment, an example in which a two-dimensional image of the identification surface is acquired using the image pickup element 19 has been described. However, in a case where the identification information is a one-dimensional code such as a barcode (registered trademark), the signal intensity from a predetermined usage region 19b like that illustrated in FIG. 28 in the pixel array 19a included in the image pickup element 19 may be graphed as illustrated in FIG. 29 while moving the image capturing unit 15 in a certain direction, for example, as illustrated in FIG. 27. In this manner, by scanning the identification surface in a certain direction and analyzing the signal from predetermined pixels of the image pickup element 19, the one-dimensional code constituting the identification information may be specified, and the specified identification information and the sample image may be recorded in association with each other.

Figure 30:
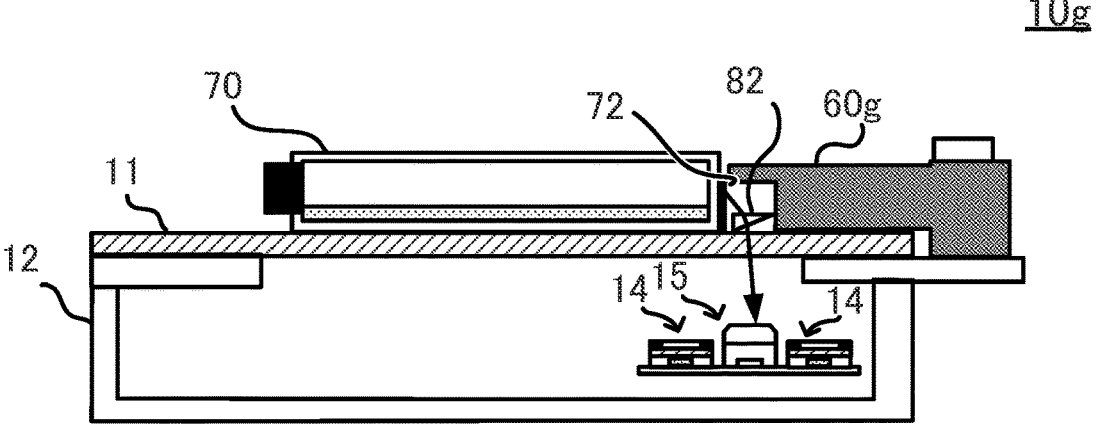
FIG. 30 is a diagram to illustrate a method with which an image capturing device images an identification surface.

FIG. 30 is a diagram to illustrate a method with which an image capturing device 10g images an identification surface. FIG. 31 is a diagram illustrating an example of an image of an identification surface captured by the image capturing device 10g. The image capturing device 10g illustrated in FIG. 30 is another modification of the image capturing device according to the third embodiment. The system according to this embodiment may also be equipped with the image capturing device 10g instead of the image capturing device 10.

In a case where the identification information is a one-dimensional code as described above, there is a case where identification information can be specified without imaging the entire identification information. Therefore, when the identification information is the one-dimensional code, the identification surface may be imaged using the image capturing device 10g in which the positioning member 60g has the wedge-shaped prism 82, as illustrated in FIG. 30.

When the identification surface is imaged via the wedge-shaped prism 82, the entire identification surface is not in focus, but part (a predetermined height portion) of the identification surface is in focus. Therefore, an image P21 in which a portion of the one-dimensional code is visualized as illustrated in FIG. 31 can be obtained. The one-dimensional code serving as the identification information may be specified by analyzing the image P21. The identification information thus specified and the image of the sample may be recorded in association with each other.

FIG. 32 is a diagram to illustrate a method with which an image capturing device 10h images an identification surface. The image capturing device 10h illustrated in FIG. 32 is yet another modification of the image capturing device according to the third embodiment. The system according to this embodiment may also be equipped with the image capturing device 10h instead of the image capturing device 10.

The image capturing device 10h differs from the image capturing device 10g in being equipped with a positioning member 60h instead of the positioning member 60g, and in that a wedge-shaped prism 83 is provided on the lower surface of the transmission window 11. Unlike the positioning member 60g, the positioning member 60h does not include the wedge-shaped prism 82, and the image capturing device 10h is equipped with a wedge-shaped prism 83 instead of the wedge-shaped prism 82.

The wedge-shaped prism 83 bonded to the lower surface of the transmission window 11 acts similarly to the wedge-shaped prism 82 provided on the upper surface of the transmission window 11. Hence, the same advantageous effects as those of the image capturing device 10g and the system including the image capturing device 10g can also be afforded by the image capturing device 10h and the system including the image capturing device 10h.

Fourth Embodiment

Figure 34:
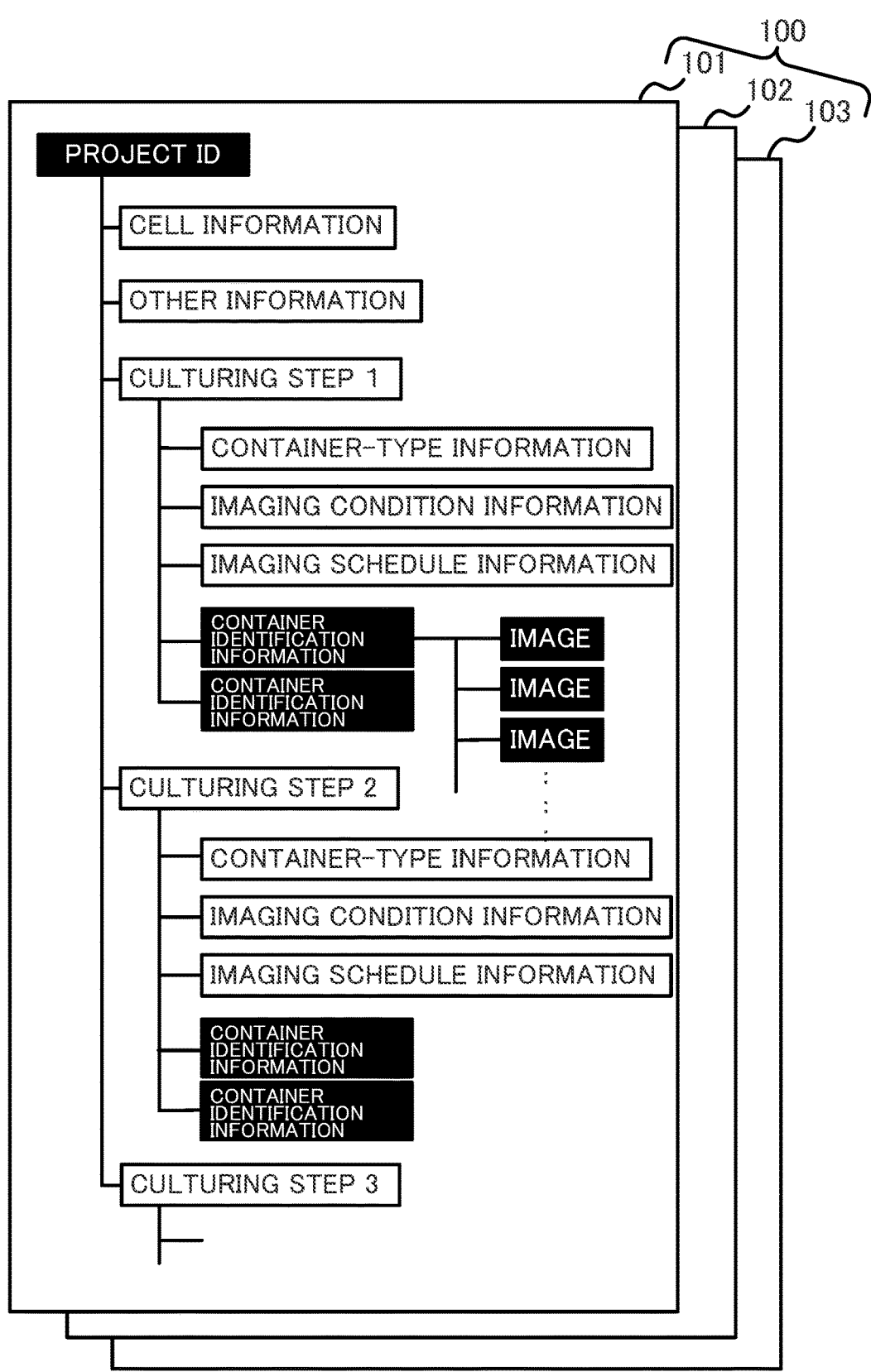
FIG. 34 is a diagram for illustrating an example of a configuration of culture information.
Figure 35:
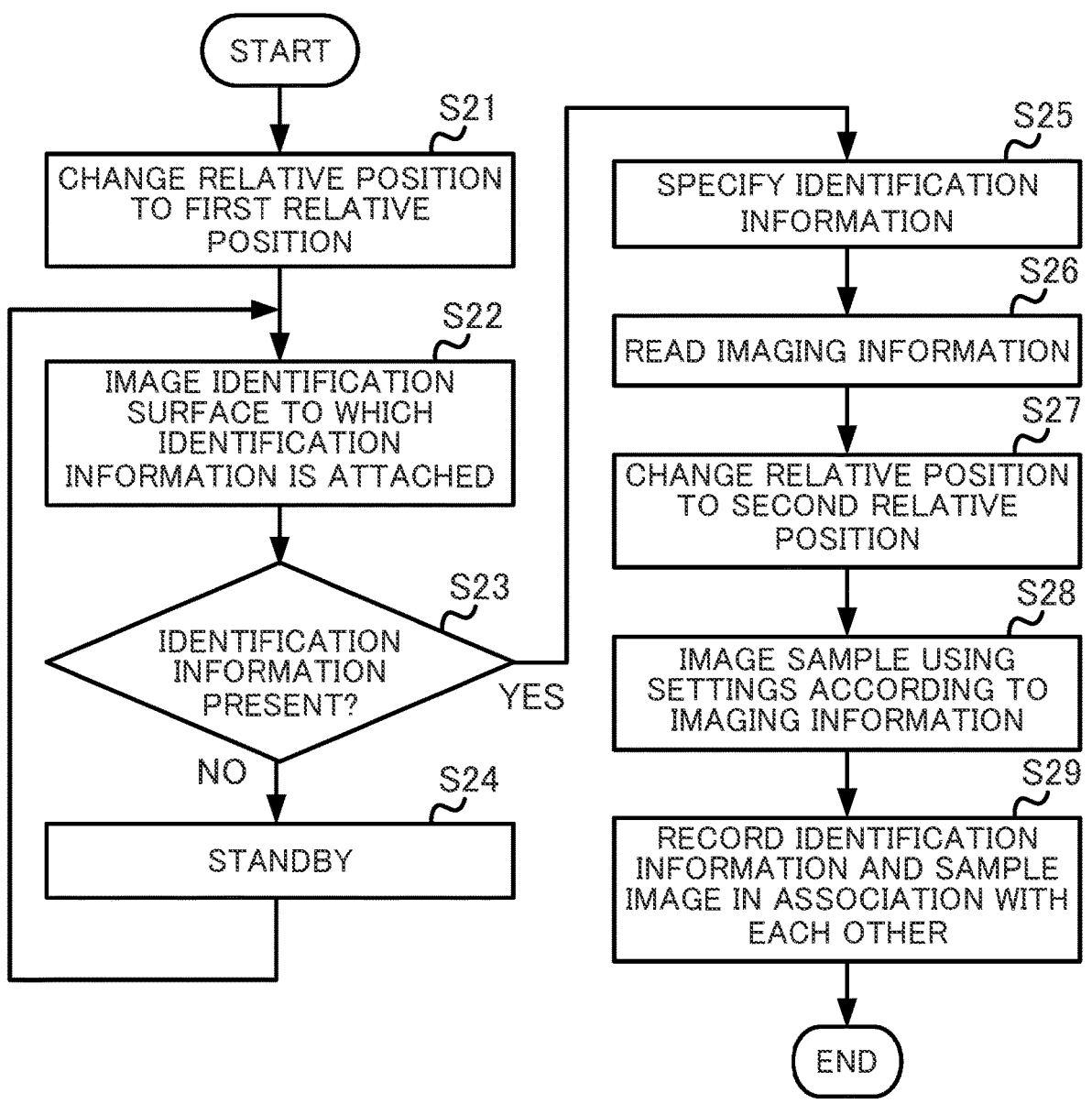
FIG. 35 is a flowchart illustrating yet another example of the processing performed by the system.

FIG. 33 is a diagram illustrating an example of a screen for registering container identification information. FIG. 34 is a diagram to illustrate an example of a configuration of culture information. FIG. 35 is a flowchart illustrating yet another example of the processing performed by the system. In the system according to the above-described embodiment, an example in which the identification information and the image of the sample are recorded in association with each other has been described. However, the system according to this embodiment differs from the system according to the above-described embodiment in that the settings of the image capturing device at the time of imaging the sample are changed on the basis of the identification information. Hereinafter, a method for changing the settings when imaging a sample according to the identification information will be specifically described with reference to FIGS. 33 to 35. Note that the system according to this embodiment is, as per the system 1, equipped with the image capturing device 10 and the control device 30.

Similarly to the system 1, the system according to this embodiment is an image capturing system that images a sample housed in a container 70 while culturing the sample. In addition, the system according to this embodiment is also an identification information issuance management system that issues and manages identification information of a container, and is also a culture project management system for managing a cell culture project.

In the system according to this embodiment which functions as an identification information issuance management system, the control device 30 may display, on a display device 34, the identification information registration screen illustrated in FIG. 33. When a user inputs information of, for example, 12 characters or less in a registration identification code field, the control device 30 generates and registers identification information such as a barcode in which the information is coded. Note that the generated identification information is registered in association with culture information, described subsequently. Furthermore, the control device 30 may print the identification information on a seal that can be attached to the container 70 by using, for example, a printing device connected to the control device 30. The user is able to attach the identification information to the container 70 by attaching the printed seal to the container 70.

Furthermore, in the system according to this embodiment that functions as a culture project management system, the control device 30 may store the culture information 100 illustrated in FIG. 34, which is information regarding a cell culture project, in the storage device 32. More specifically, the culture information 100 (culture information 101, culture information 102, and culture information 103 . . . ) is created for each cell culture project. As illustrated in FIG. 34, the culture information 100 includes information on the cultured cells (cell information), other information, and information on each culturing step in advance, in association with a project ID for identifying a project. Furthermore, the information on each culturing step includes, for example, information on the type of container to be used (container-type information), information on imaging conditions when imaging the cultured cells constituting the sample (imaging condition information), information on a schedule for imaging the cultured cells (imaging schedule information), and information for specifying the culture container to be used for imaging (the container identification information is also simply referred to as identification information.). Note that the imaging condition information and the imaging schedule information are collectively referred to as imaging information. In other words, the information on each culturing step includes, for example, container-type information, imaging information, and container identification information. Here, the container identification information is information obtained by encoding the registered identification code or the registered identification code registered on the identification information registration screen illustrated in FIG. 33. In the system according to this embodiment, when a sample is imaged, an image of the sample is recorded as part of the culture information 100 in association with the container identification information, as illustrated in FIG. 34.

In the system according to this embodiment, a program stored in the storage device 32 is executed by the processor 31, and the processing illustrated in FIG. 35 is performed. When the processing illustrated in FIG. 35 is started, the system first changes the relative position to the first relative position (step S21), and images the identification surface to which the identification information is attached (step S22). These processing steps are the same as the processing of steps S1 and S2 of FIG. 7.

Next, the system determines whether the identification information is included in the image of the identification surface captured in step S22 (step S23), and when the identification information is not included (step S23: NO), the system stands by for a certain period of time (step S24), and then repeats the processing of steps S22 and S23. Note that a situation in which the culture container is removed from the incubator 20 and an operation such as culture medium replacement is performed may be considered as a situation in which the identification information is not included, for example. By repeating the processing while waiting for a certain period of time, the operation is completed, and the culture container placed in the incubator 20 can be imaged again, and hence the identification information can be detected in step S23.

When it is determined that the identification information is included (step S23: YES), the system specifies the identification information (step S25). Here, the control device 30 analyzes the image of the identification surface captured in step S22 and specifies the identification information included in the image.

Further, the system reads the imaging information indicating the settings of the image capturing device (step S26). Here, the control device 30 reads imaging information associated with the identification information specified in step S25 from the culture information 100 stored in the storage device 32. Note that the imaging information refers to general information used by the image capturing device 10 to image a sample, and includes imaging condition information and imaging schedule information that are stored in the storage device 32 in association with identification information, as illustrated in FIG. 34, for example.

When the imaging information is read, the system changes the relative position to the second relative position (step S27). This processing is the same as the processing of step S3 of FIG. 7.

Thereafter, the system images the sample using settings according to the imaging information (step S28). Here, the control device 30 changes the settings of the image capturing device 10 according to the imaging information read in step S26. Specifically, for example, the control device 30 may change the imaging coordinates according to the imaging condition information included in the imaging information, may switch the light source units 14 to be used, or may change the illumination intensity. Furthermore, for example, the control device 30 may change the settings for the imaging time, the number of imaging actions, and the like, according to the imaging schedule information included in the imaging information. After the settings are changed, the control device 30 then transmits an imaging instruction to the image capturing device 10 to cause the image capturing device 10 to image the sample using the settings according to the imaging information.

When the imaging of the sample is completed, the system records the identification information and the image of the sample in association with each other (step S29). Here, the control device 30 stores the image of the sample generated in step S28 in the storage device 32 in association with the identification information specified in step S25.

The image capturing device and the system according to this embodiment also enable the identification information attached to the container 70 and the image of the sample housed in the container 70 to be recorded in association with each other by performing the processing illustrated in FIG. 35, similarly to the image capturing device 10 and the system 1 according to the first embodiment. Furthermore, the same is also true regarding the fact that the identification information can be acquired without providing a dedicated camera or the like for imaging the identification surface, the fact that the presence of the identification information adversely affects the imaging of the sample is avoidable, and the fact that the user is able to install the light guide unit in an appropriate position simply by performing work using a conventional procedure.

According to the image capturing device and the system according to this embodiment, it is possible to image a sample according to imaging information stored in advance as culture information in association with the identification information, on the basis of the identification information. Further, the image generated by the imaging is recorded as culture information in association with the identification information. Therefore, it is possible to easily realize centralized management of various types of information in cell culture, and automatic imaging of cultured cells according to the managed information.

Fifth Embodiment

Figure 36:
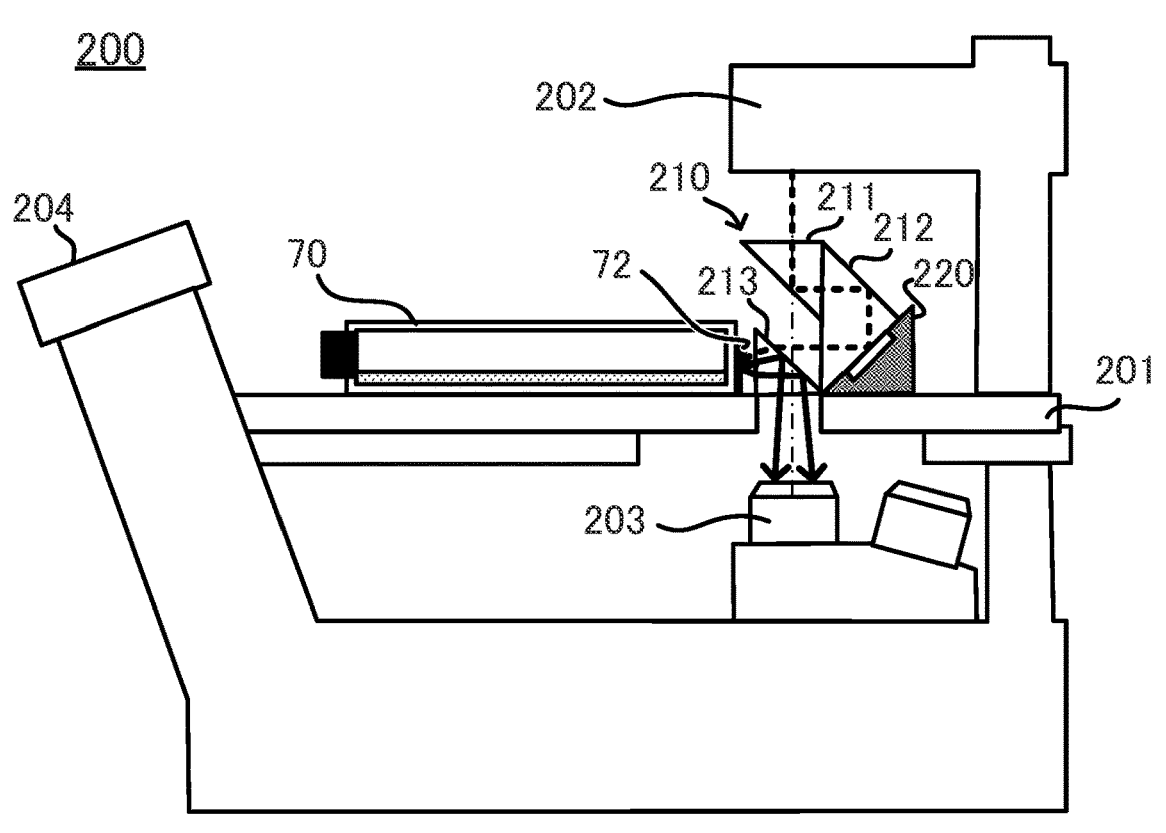
FIG. 36 is a diagram to illustrate a method with which a microscope images an identification surface.
Figure 37:
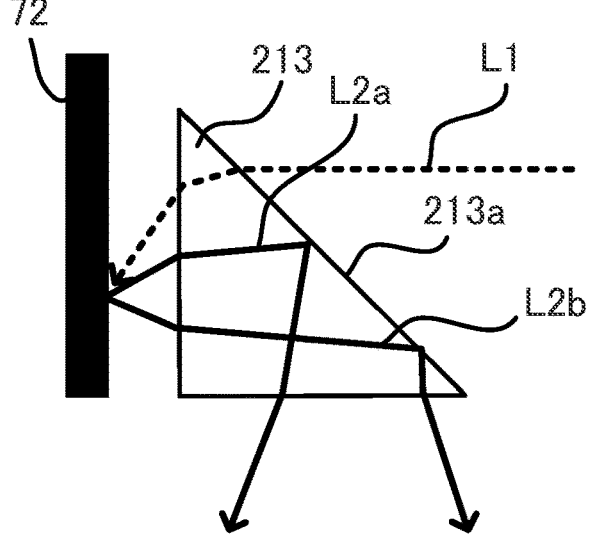
FIG. 37 is a diagram to illustrate the action of a prism.

FIG. 36 is a diagram to illustrate a method with which a microscope 200 images an identification surface. FIG. 37 is a diagram to illustrate the action of a prism 213. In the system according to the above-described embodiment, an example is illustrated in which the image capturing device used in the incubator 20 is included as the image capturing device, but the image capturing device included in the system is not limited to the image capturing device used in the incubator 20. The system according to this embodiment differs from the system according to the above-described embodiment in that an inverted microscope is included as an image capturing device for imaging a sample. Hereinafter, the microscope 200 included in the system according to this embodiment will be specifically described with reference to FIGS. 36 and 37.

The microscope 200 is an inverted microscope that includes an eyepiece 204, and is an image capturing device corresponding to imaging in addition to visual observation. The microscope 200 includes an image pickup element (not illustrated), and images a sample from below the container 70. More specifically, as illustrated in FIG. 36, the microscope 200 includes a stage 201, a light source 202 for transmitted illumination, an objective 203, the eyepiece 204, and an image pickup element (not illustrated). In the microscope 200, the image pickup element and the objective 203 constitute an image capturing unit. The stage 201 is an electric stage that moves according to an instruction from the control device 30, and is a mobile unit that changes a relative position of the image capturing unit with respect to the container 70.

In the microscope 200, when the sample is imaged, the stage 201 moves the relative position to the second relative position in which the optical axis of the objective 203 intersects with the container 70. The microscope 200 then captures an image of the sample through the bottom surface of the container 70.

The microscope 200 further includes an auxiliary optical system 210 that is installed on the stage 201 together with the container 70; a support member 220 that supports the auxiliary optical system 210; and a prism 213. The prism 213 is a light guide unit that guides the light from the identification surface to the image capturing unit, and is a total reflection prism that totally reflects the light from the identification surface toward the objective 203.

As illustrated in FIG. 36, the auxiliary optical system 210 is configured from a plurality of prisms (prism 211, and prism 212), and guides illumination light from the light source 202 of the microscope 200 to the identification surface via the prism 213 constituting a light guide unit.

In the microscope 200, when the identification surface is imaged, the stage 201 moves the relative position to the first relative position in which the optical axis of the objective 203 deviates from the container 70. Specifically, the stage 201 moves the prism 213, which moves together with container 70, onto the optical axis of the image capturing unit (objective 203) as illustrated in FIG. 36. The microscope 200 then captures an image of the identification surface through the prism 213. Specifically, as illustrated in FIG. 37, the illumination light L1 parallel to the stage 201 falls incident on the prism 213 through the auxiliary optical system 210, and is then refracted by the prism 213 and illuminates the identification surface to which the identification information 72 is attached. Of the light from the identification surface illuminated with the illumination light L1, the light (light L2a) emitted vertically upward from the horizontal direction falls incident upon an inclined surface 213a at a relatively small incident angle. Therefore, only light falling incident upon the inclined surface 213a at an angle larger than the critical angle is reflected by the inclined surface 213a and guided toward the image capturing unit. Meanwhile, of the light from the identification surface illuminated with the illumination light L1, the light (light L2b) emitted vertically downward from the horizontal direction falls incident upon the inclined surface 213a at a relatively large incident angle and hence is reflected by the inclined surface 213a and falls incident upon the objective 203. In this manner, the light incident on the objective 203 forms an optical image of the identification surface, on the image pickup element.

The microscope 200 and the system including the microscope 200 according to this embodiment also enable the identification information attached to the container 70 and the image of the sample housed in the container 70 to be recorded in association with each other by performing the processing illustrated in FIG. 7, similarly to the image capturing device 10 and the system 1 according to the first embodiment. Furthermore, the same is also true regarding the fact that the identification information can be acquired without providing a dedicated camera or the like for imaging the identification surface, the fact that the presence of the identification information adversely affects the imaging of the sample is avoidable, and the fact that the user is able to install the light guide unit in an appropriate position simply by performing work using a conventional procedure. Accordingly, the same advantageous effects as those of the image capturing device 10 and the system 1 according to the first embodiment can be afforded.

Figure 38:
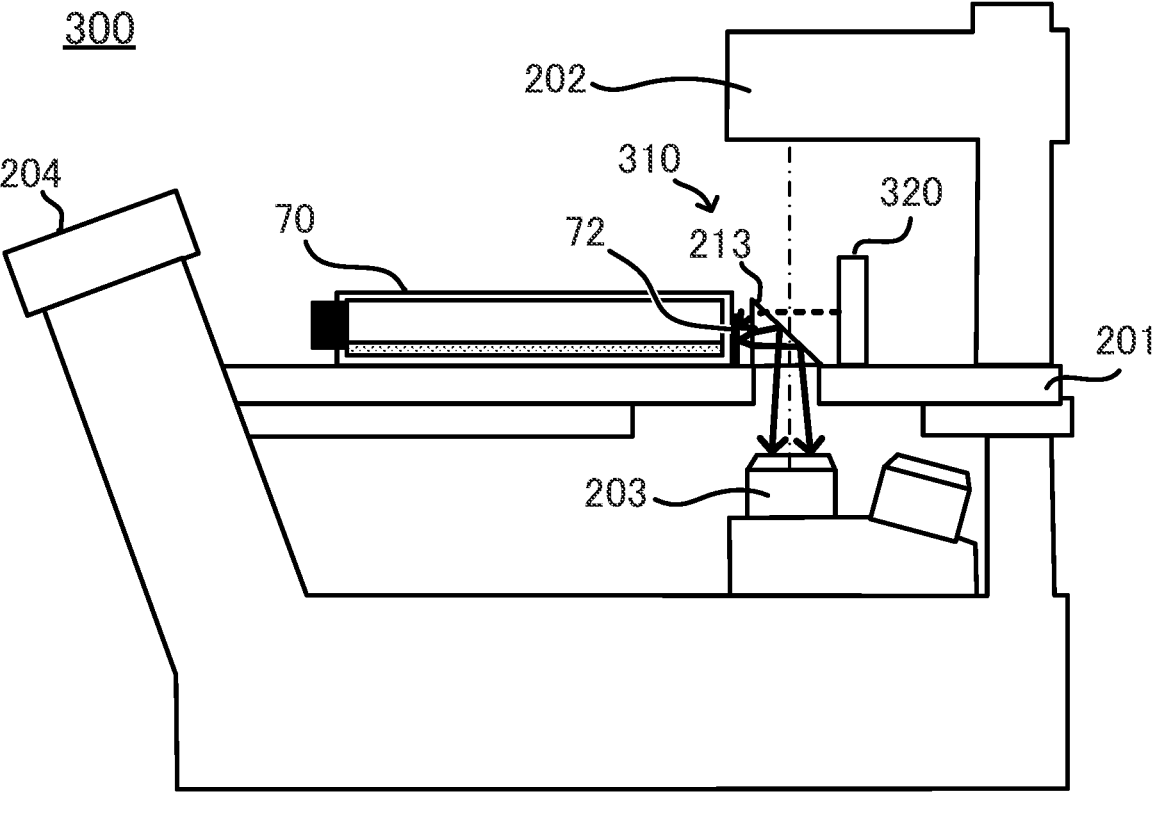
FIG. 38 is a diagram to illustrate a method with which a microscope images an identification surface.

FIG. 38 is a diagram to illustrate a method with which a microscope 300 images an identification surface. A microscope 300 illustrated in FIG. 38 is a modification of the image capturing device according to a fifth embodiment. The system according to this embodiment may include a microscope 300 instead of the microscope 200.

The microscope 300 differs from the microscope 200 in including an auxiliary light source 320 instead of the auxiliary optical system 210 and the support member 220. In the microscope 200, the light from the light source 202 is converted into light approximately parallel to the stage 201 by using the auxiliary optical system 210, and the identification surface is irradiated with the light via the prism 213. Meanwhile, in the microscope 300, illumination similar to that of the microscope 200 can be realized by causing the illumination light to directly enter the prism 213 from the auxiliary light source 320.

Therefore, the same advantageous effects as those of the image capturing device 10 and the system 1 according to the first embodiment can be afforded by the microscope 300 and the system including the microscope 300.

The above-described embodiments are specific examples to facilitate an understanding of the invention, and hence the present invention is not limited to such embodiments. Modifications obtained by modifying the above-described embodiments and alternatives to the above-described embodiments may also be included. That is, the constituent elements of each embodiment can be modified without departing from the spirit and scope of the embodiment. Moreover, new embodiments can be implemented by appropriately combining a plurality of constituent elements disclosed in one or more of the embodiments. Furthermore, some constituent elements may be omitted from the constituent elements in each embodiment, or some constituent elements may be added to the constituent elements in each embodiment. Further, the order of the processing procedure disclosed in each embodiment may be changed as long as no contradiction results. In other words, the image capturing device, the image capturing system, and the control method of the present invention can be variously modified and altered without departing from the scope of the patent claims.

Figure 39:
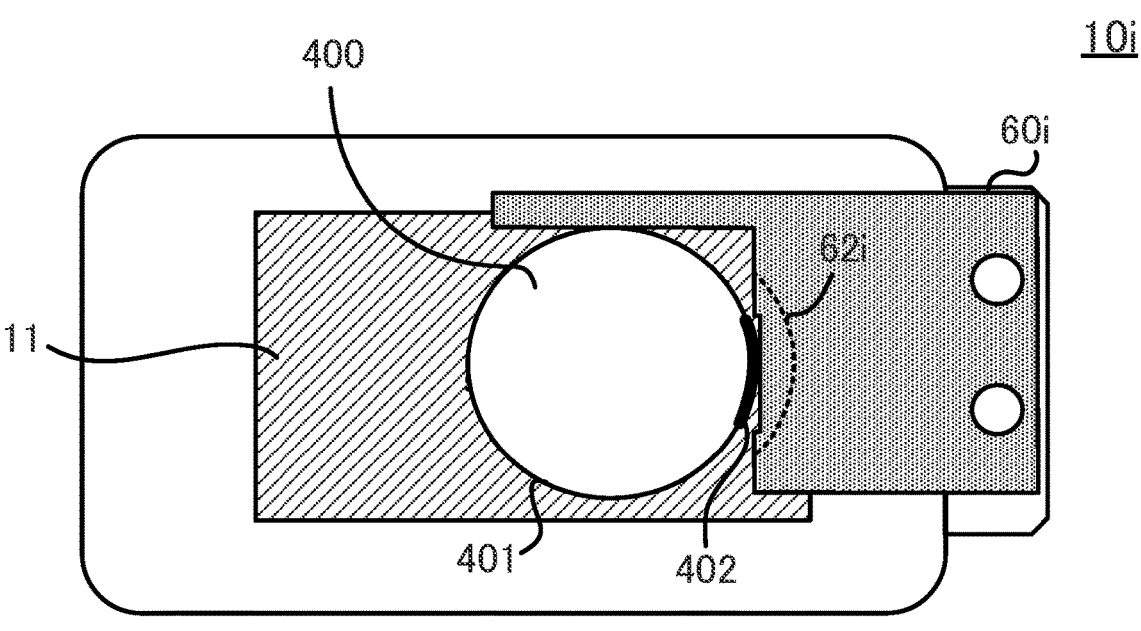
FIG. 39 is a diagram to illustrate a method with which an image capturing device images an identification surface.

In the above-described embodiments, an example in which the lateral surface of the container is a flat surface has been described. However, the lateral surface of the container may be configured by, for example, a curved surface, as illustrated in FIG. 39. In such a case, an image capturing device 10i that includes a positioning member 60i in which a deflection surface 62i is configured from a curved surface having the same curvature as the lateral surface may be used. Further, the lateral surface of the container used as the identification surface may be inclined. In particular, when the reduction optical system is included in the light guide unit, the depth of focus becomes deep, and hence the identification information can be adequately acquired even when the lateral surface is inclined. In addition, the identification surface is not limited to the lateral surface of the container, and may be, for example, the upper surface of the container. In this case, the light guide unit may generate a detour in the optical path so that the identification surface can be observed from above the container.

Figure 40:
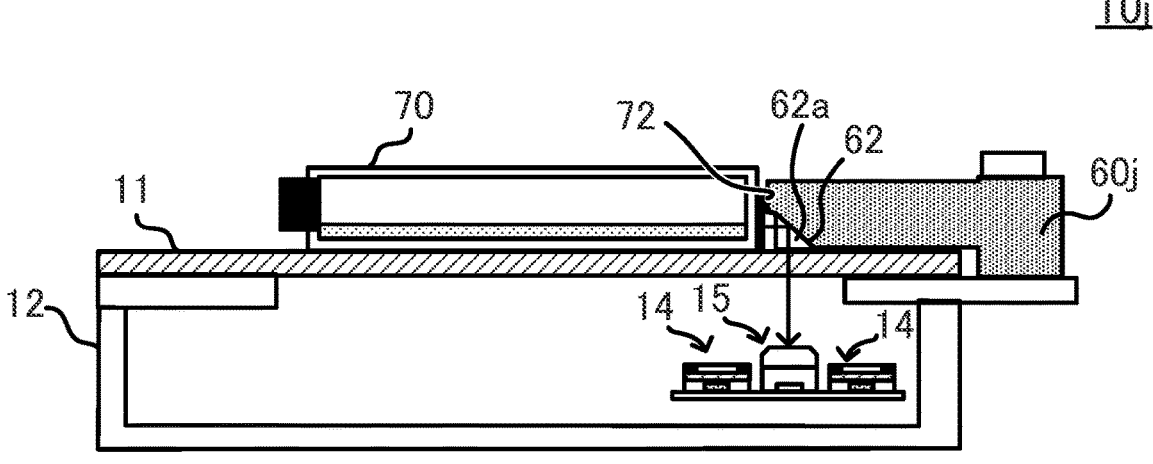
FIG. 40 is a diagram to illustrate a method with which an image capturing device images an identification surface.

Furthermore, although, in the above-described embodiment, an example was described in which a bypass in the optical path is made in order to gain optical path length, a member having a high refractive index such as a prism may be inserted into the optical path to gain optical path length, for example. For example, as illustrated in FIG. 40, by using an image capturing device 10j that includes a positioning member 60j in which a prism 62a is provided immediately before the deflection surface 62, it is possible to eliminate the optical path length difference from the image pickup element 19 to the imaging object in the first and second relative positions.

What is claimed is:

1. An image capturing device for observing a sample housed in a container to which identification information is attached, from below the container, the image capturing device comprising:

an image capturing unit including an image pickup element;

a light guide unit that guides light from an identification surface to the image capturing unit, the identification surface being a surface of the container which differs from a bottom surface of the container and to which the identification information is attached; and a mobile unit that changes a relative position of the image capturing unit with respect to the container, wherein, after the mobile unit changes the relative position to a first relative position in which an optical axis of the image capturing unit deviates from the container, the image capturing unit images the identification surface via the light guide unit, and after the mobile unit changes the relative position to a second relative position in which the optical axis of the image capturing unit intersects the container, the image capturing unit images the sample via the bottom surface.

2. The image capturing device according to claim 1, wherein the light guide unit includes a reduction optical system that reduces a projection magnification between the identification surface and the image pickup element.

3. The image capturing device according to claim 2, wherein the reduction optical system is a relay optical system that forms an intermediate image of the identification surface.

4. The image capturing device according to claim 2, further comprising:

a housing that has a placement surface whereon the container is placed and that houses the image capturing unit and the mobile unit; and a positioning member that is fixed to the housing and that positions the container on the placement surface, wherein the positioning member includes at least part of the light guide unit.

5. The image capturing device according to claim 2, wherein the image capturing device is an inverted microscope, and upon changing the relative position to the first relative position, the mobile unit moves the light guide unit, which moves together with the container, on the optical axis of the image capturing unit.

6. The image capturing device according to claim 1, further comprising:

a housing that has a placement surface whereon the container is placed and that houses the image capturing unit and the mobile unit; and a positioning member that is fixed to the housing and that positions the container on the placement surface, wherein the positioning member includes at least part of the light guide unit.

7. The image capturing device according to claim 6, wherein the positioning member includes a reduction optical system that reduces a projection magnification between the identification surface and the image pickup element.

8. The image capturing device according to claim 6, wherein the identification surface is a lateral surface of the container facing the positioning member.

9. The image capturing device according to claim 1, wherein the image capturing device is an inverted microscope, and upon changing the relative position to the first relative position, the mobile unit moves the light guide unit, which moves together with the container, on the optical axis of the image capturing unit.

10. The image capturing device according to claim 9, further comprising:

an auxiliary optical system that guides illumination light from a light source of the inverted microscope to the identification surface via the light guide unit.

11. The image capturing device according to claim 9, further comprising:

an auxiliary light source that illuminates the identification surface via the light guide unit.

12. The image capturing device according to claim 1, further comprising:

a control device that controls operation of the image capturing unit and the mobile unit, wherein the control device performs control in which the identification surface is imaged by the image capturing unit after the relative position is changed to the first relative position by controlling the mobile unit, and performs control in which the sample is imaged by the image capturing unit after the relative position is changed to the second relative position by controlling the mobile unit.

13. An image capturing system, comprising:

the image capturing device according to claim 1; and a control device that controls operation of the image capturing unit and the mobile unit, wherein the control device records the identification information and the image of the sample in association with each other.

14. The image capturing system according to claim 13, wherein the control device includes a storage unit that stores imaging information in association with the identification information, specifies the identification information from the image of the identification surface captured by the image capturing device in the first relative position, reads, from the storage unit, the imaging information associated with the specified identification information, and causes the image capturing device to image the sample in the second relative position by using a setting corresponding to the imaging information thus read.

15. The image capturing system according to claim 13, wherein the control device causes the image capturing device to image the identification surface in a plurality of different first relative positions, combines the plurality of identification-surface images captured in the plurality of first relative positions to generate a composite image in which the entire identification information is captured, and specifies the identification information based on the composite image.

16. An image capturing system, comprising:

the image capturing device according to claim 2; and a control device that controls operation of the image capturing unit and the mobile unit, wherein the control device records the identification information and the image of the sample in association with each other.

17. A control method for an image capturing device that is equipped with an image capturing unit and a mobile unit that changes a relative position of the image capturing unit with respect to a container housing a sample, the method comprising:

changing the relative position to a first relative position in which an optical axis of the image capturing unit deviates from the container;

imaging an identification surface via a light guide unit that guides light from the identification surface to the image capturing unit, the identification surface being a surface of the container which differs from a bottom surface of the container and to which identification information is attached;

changing the relative position to a second relative position in which the optical axis of the image capturing unit intersects the container; and imaging the sample via the bottom surface.

18. The control method according to claim 17, further comprising:

changing settings of the image capturing device based on the identification information specified from the captured image of the identification surface.

19. The control method according to claim 17, wherein changing to the first relative position includes sequentially changing to a plurality of different first relative positions, imaging the identification surface includes imaging the identification surface in each of the plurality of first relative positions, the control method further comprising:

changing the settings of the image capturing device based on the identification information specified from a composite image obtained by combining the plurality of identification-surface images captured in the plurality of first relative positions.

20. The control method according to claim 17, wherein imaging the identification surface includes:

forming an intermediate image of the identification surface that is obtained by the identification surface being reduced by a reduction optical system included in the light guide unit; and forming a projection image of the identification surface that is obtained by the intermediate image being enlarged by the image capturing unit.

\* \* \* \* \*